US012608448B1

(12) United States Patent
Busch et al.

(10) Patent No.: US 12,608,448 B1
(45) Date of Patent: Apr. 21, 2026

(54) APPLIED COMPUTER TECHNOLOGY FOR AUTONOMOUS AND RECURSIVE CLUSTER-BASED GENETIC FAMILY TREE CONSTRUCTION BASED ON MEASURES OF GENETIC RELATEDNESS AMONG INDIVIDUALS

(71) Applicant: Indago Solutions LLC, Upland, CA (US)

(72) Inventors: Stephen Thomas Busch, Upland, CA (US); Robert Stephen Kramer, Upland, CA (US); James Vinall, Upland, CA (US)

(73) Assignee: Indago Solutions LLC, Upland, CA (US)

( * ) Notice: Subject to any disclaimer, the term of this patent is extended or adjusted under 35 U.S.C. 154(b) by 0 days.

(21) Appl. No.: 18/535,593

(22) Filed: Dec. 11, 2023

Related U.S. Application Data

(60) Provisional application No. 63/432,623, filed on Dec. 14, 2022, provisional application No. 63/387,042, filed on Dec. 12, 2022.

(51) Int. Cl.
*G06F 16/22* (2019.01)
*G06F 18/2323* (2023.01)
*G16B 40/00* (2019.01)

(52) U.S. Cl.
CPC .......... *G06F 18/2323* (2023.01); *G06F 16/22* (2019.01); *G16B 40/00* (2019.02)

(58) Field of Classification Search
CPC ...... G06F 18/2323; G06F 16/22; G16B 40/00

USPC ......................................................... 707/737
See application file for complete search history.

(56) References Cited

U.S. PATENT DOCUMENTS

| | | | |
|---|---|---|---|
| 10,635,680 | B2 | 4/2020 | Jiang et al. |
| 11,170,257 | B2 | 11/2021 | Li et al. |
| 11,416,501 | B2 | 8/2022 | Jiang et al. |
| 11,429,615 | B2 | 8/2022 | Song et al. |
| 2021/0166452 | A1* | 6/2021 | Jewett .................... G16B 10/00 |

(Continued)

OTHER PUBLICATIONS

Bettinger, "Figure 1. The Relationship Chart", The Shared cM Project—Version 3.0, Aug. 2017, 1 page, www.geneticgenealogist. com.

(Continued)

*Primary Examiner* — Michael Pham
(74) *Attorney, Agent, or Firm* — Thompson Coburn LLP

(57) ABSTRACT

One or more genetic family trees are formed that connect a plurality of individuals based on measures of genetic relatedness between the individuals. A plurality of the individuals are grouped into a cluster that comprises those individuals who are genetically related to (1) a target individual according to first data and (2) each other according to second data. The first data comprises genetic relatedness measures for a plurality of the individuals relative to the target individual, and the second data comprises genetic relatedness measures between a plurality of the individuals. The cluster is deconstructed into a tree structure based on the first data, and family tree(s) are iteratively formed based on pairs of adjacent nodes from the tree structure until the nodes are positioned in family tree(s) based on the second data. The family tree(s) can be connected to the target individual based on the first data.

24 Claims, 18 Drawing Sheets

110

200: Identify target for whom family tree is to be constructed

202: Group individuals into clusters based on measures of genetic relatedness to the identified target and between individuals so that each cluster comprises (1) individuals genetically related to the identified target and (2) individuals genetically related to each other 204: Deconstruct the clusters into tree structure(s) where the nodes of the tree structure(s) represent corresponding individuals from the clusters so that each tree structure comprises nodes that are hierarchically arranged based on measures of genetic relatedness for the corresponding individuals to the identified target 206: Recursively process the tree structure(s) to build a family tree for identified target based on (1) measures of genetic relatedness between the corresponding individuals for groups of nodes in the tree structures and (2) measures of genetic relatedness relative to the identified target

(56)        References Cited

U.S. PATENT DOCUMENTS

2023/0116793 A1 *   4/2023   Song ..................... G16B 40/20
                                                    702/19
2023/0161796 A1 *   5/2023   Wilson ................. G06F 3/0482
                                                    707/736
2023/0342364 A1 *   10/2023  Pavlovic ............ G06F 16/2465

OTHER PUBLICATIONS

Bettinger, "Table 1. The Cluster Chart", The Shared cM Project—
Version 3.0, Aug. 2017, 1 page, www.geneticgenealogist.com.

* cited by examiner

Figures 2, 3A:
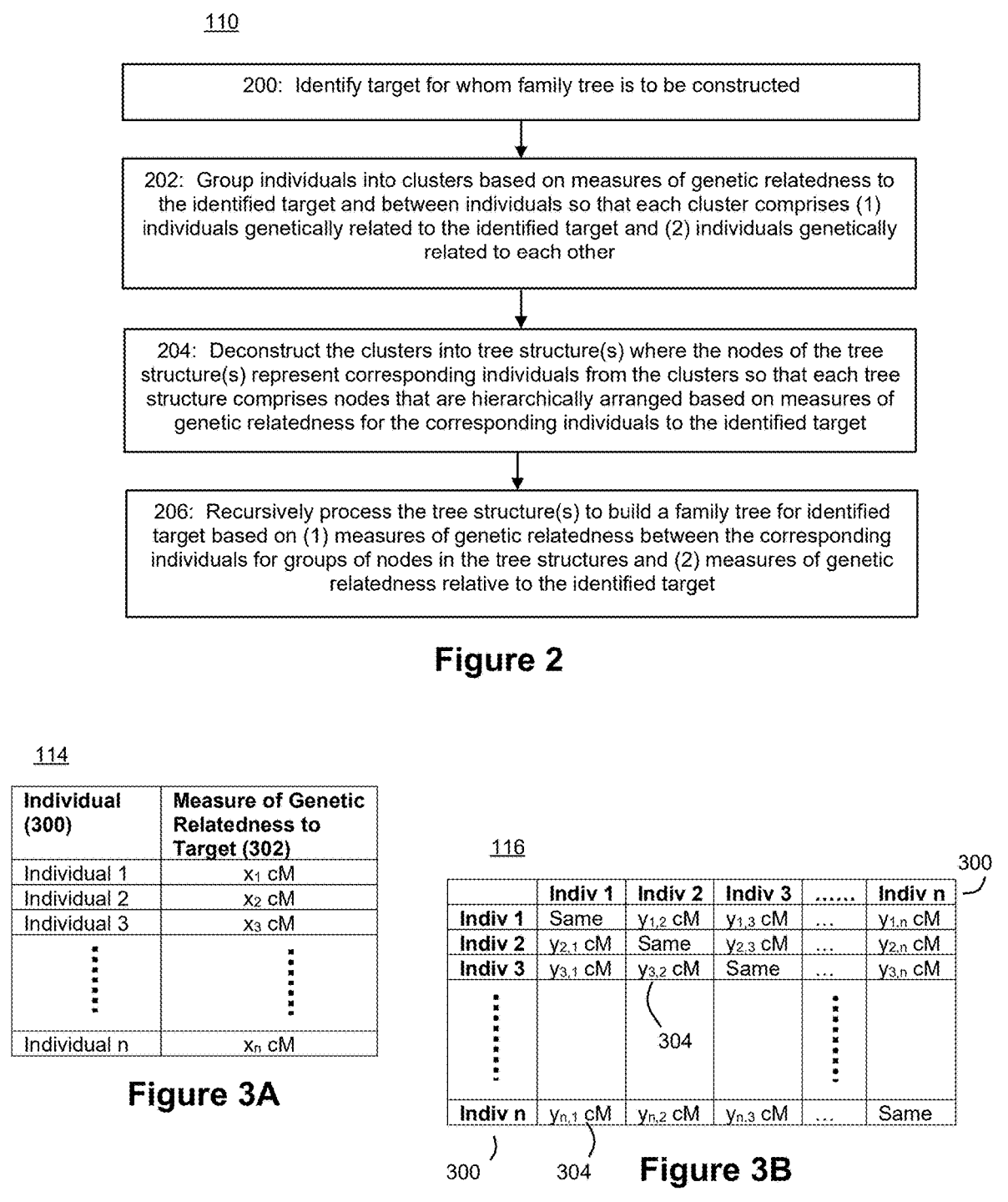

110

| 200: Identify target for whom family tree is to be constructed |

↓

| 202: Group individuals into clusters based on measures of genetic relatedness to the identified target and between individuals so that each cluster comprises (1) individuals genetically related to the identified target and (2) individuals genetically related to each other |

↓

| 204: Deconstruct the clusters into tree structure(s) where the nodes of the tree structure(s) represent corresponding individuals from the clusters so that each tree structure comprises nodes that are hierarchically arranged based on measures of genetic relatedness for the corresponding individuals to the identified target |

↓

| 206: Recursively process the tree structure(s) to build a family tree for identified target based on (1) measures of genetic relatedness between the corresponding individuals for groups of nodes in the tree structures and (2) measures of genetic relatedness relative to the identified target |

| Individual (300) | Measure of Genetic Relatedness to Target (302) |
|---|---|
| Individual 1 | $x_1$ cM |
| Individual 2 | $x_2$ cM |
| Individual 3 | $x_3$ cM |
| ⋮ | ⋮ |
| Individual n | $x_n$ cM |

| | Indiv 1 | Indiv 2 | Indiv 3 | ...... | Indiv n |
|---|---|---|---|---|---|
| Indiv 1 | Same | $y_{1,2}$ cM | $y_{1,3}$ cM | ... | $y_{1,n}$ cM |
| Indiv 2 | $y_{2,1}$ cM | Same | $y_{2,3}$ cM | ... | $y_{2,n}$ cM |
| Indiv 3 | $y_{3,1}$ cM | $y_{3,2}$ cM | Same | ... | $y_{3,n}$ cM |
| ⋮ | ⋮ | 304 | | ⋮ | |
| Indiv n | $y_{n,1}$ cM | $y_{n,2}$ cM | $y_{n,3}$ cM | ... | Same |

300      304      Figure 3B

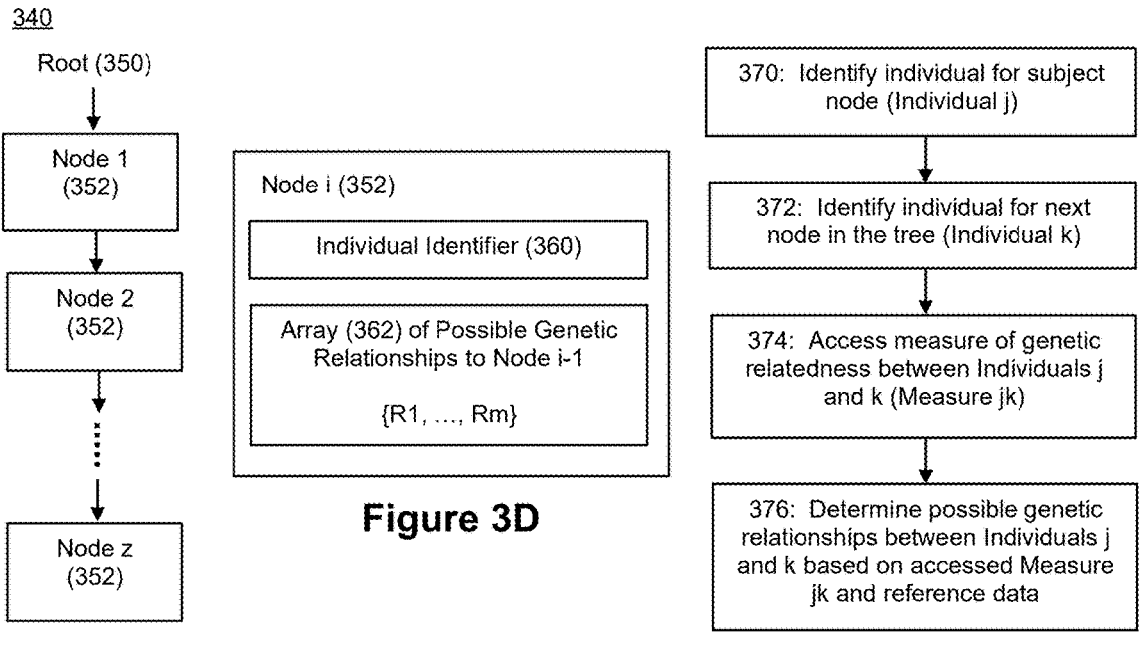

340

Root (350)

Node 1
(352)

Node 2
(352)

Node z
(352)

Figure 3C

Node i (352)

Individual Identifier (360)

Array (362) of Possible Genetic
Relationships to Node i-1

370: Identify individual for subject
node (Individual j)

372: Identify individual for next
node in the tree (Individual k)

374: Access measure of genetic
relatedness between Individuals j
and k (Measure jk)

376: Determine possible genetic
relationships between Individuals j
and k based on accessed Measure
jk and reference data

| Relationship to Individual (e.g., Parent of Individual, Child of Individual, etc.) | cM Distance Range | Average cM Distance |
|---|---|---|
| Parent (P) | 3325-3725 | 3500 |
| Child (C) | 3325-3725 | 3500 |
| Sibling (S) | 2220-3390 | 2630 |
| Half Sibling (HS) | 1310-2315 | 1780 |
| Grandparent (GP) | 1150-2315 | 1765 |
| Grandchild (GC) | 1150-2315 | 1765 |
| Aunt/Uncle (AU) | 1350-2175 | 1750 |
| Niece/Nephew (NN) | 1350-2175 | 1750 |
| Great Aunt/Uncle (GAU) | 250-2105 | 915 |
| Great Niece/Nephew (GNN) | 250-2105 | 915 |
| Half Aunt/Uncle (HAU) | 500-1445 | 890 |
| Half Niece/Nephew (HNN) | 500-1445 | 890 |
| Great Grandparent (GGP) | 465-1485 | 880 |
| First Cousin (C1) | 550-1225 | 875 |
| Half First Cousin (HC1) | 135-855 | 460 |
| First Cousin Once Removed (1C1R) | 140-850 | 440 |
| Half First Cousin Once Removed (H1C1R) | 55-530 | 225 |
| ⋮ | ⋮ | ⋮ |

Figure 3F

See "Comp - Tree Validity"
See "Comp - MCRA Builder"
See "Comp - Tree Probability Weight"

Comp - MCRA Builder

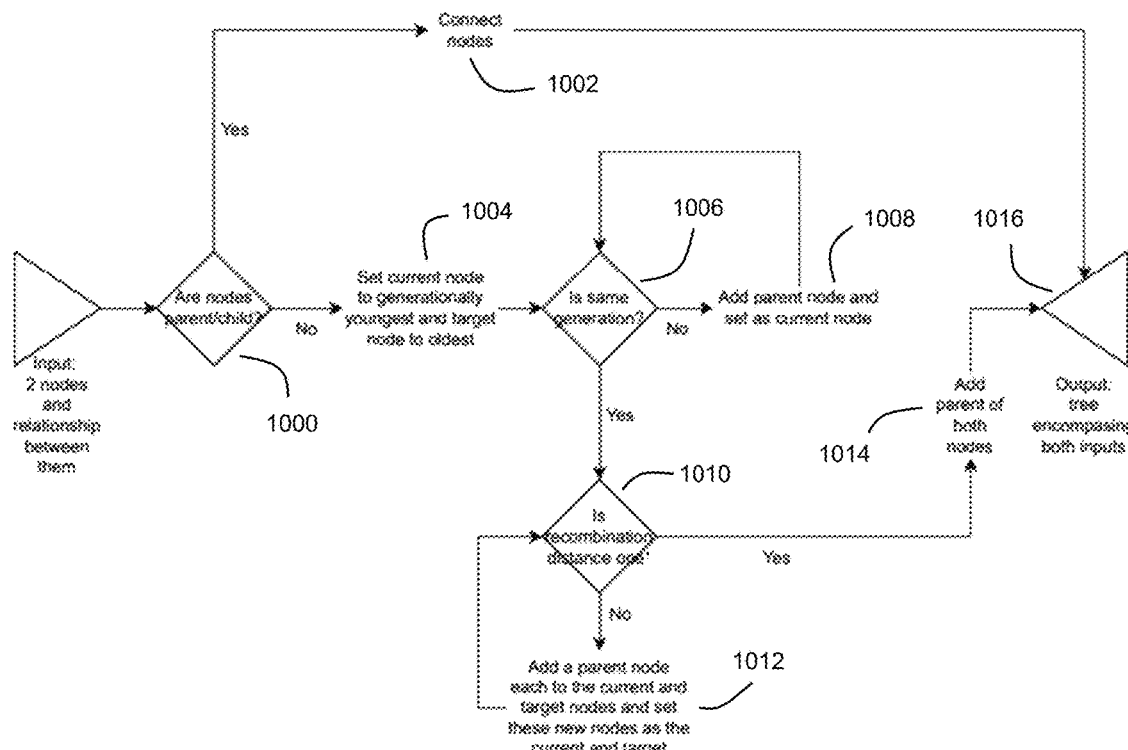

Figure 10

'All relationships are assigned a generational distance and a recombination (or MCRA) distance. For relationships at a generational distance of zero, the recombination distance describes the number of times a recombination event needed to happen for shared ancestry (this is basically a distance to the MRCA) with zero meaning they share a parent.

Comp - Tree Probability Weight

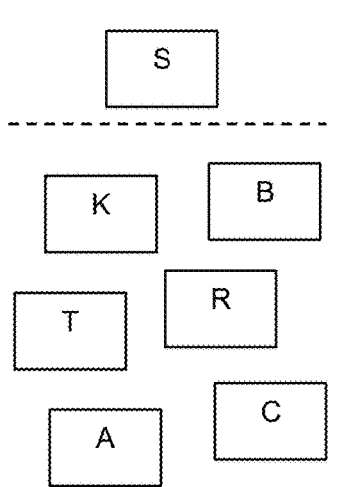
Figure 12
114
| Individual (300) | cM Distance Relative to Primary (S) (302) |
|---|---|
| K | 1705 cM |
| B | 1695 cM |
| T | 875 cM |
| R | 870 cM |
| A | 450 cM |
| C | 225 cM |
Figure 13
116
| | K | B | T | R | A | C |
|---|---|---|---|---|---|---|
| K | Same | --- | --- | 3405 cM | 3395 cM | 1750 cM |
| B | --- | Same | 3400 cM | --- | --- | --- |
| T | --- | 3400 cM | Same | --- | --- | --- |
| R | 3405 cM | --- | --- | Same | 1800 cM | 1700 cM |
| A | 3395 cM | --- | --- | 1800 cM | Same | 3380 cM |
| C | 1750 cM | --- | --- | 1700 cM | 3380 cM | Same |
Figure 14
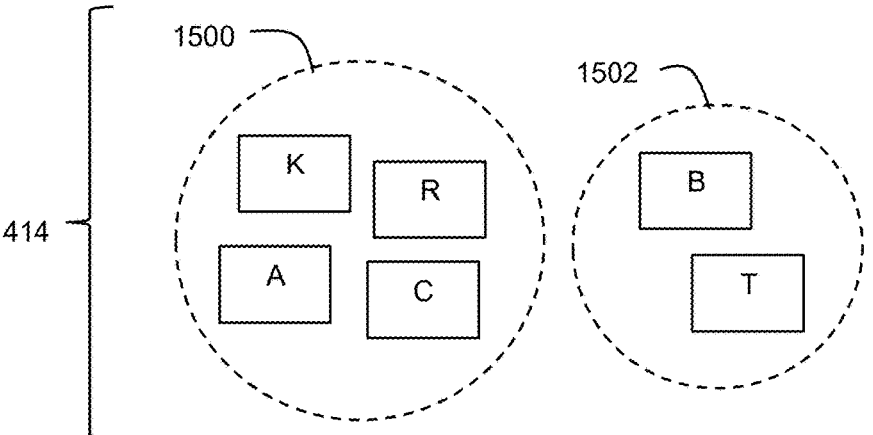
Figure 15

| Node | Next Node Up | Array of Possible Genetic Relationships to Next Node Up (362) |
|---|---|---|
| K | Root | NA |
| R | K | {Parent, Child} |
| A | R | {Aunt/Uncle, Half Sibling, Niece/Nephew, Grandparent, Grandchild, Great Aunt/Uncle, Great Niece/Nephew} |
| C | A | {Parent. Child, Sibling} |
| B | Root | NA |
| T | B | {Parent, Child} |

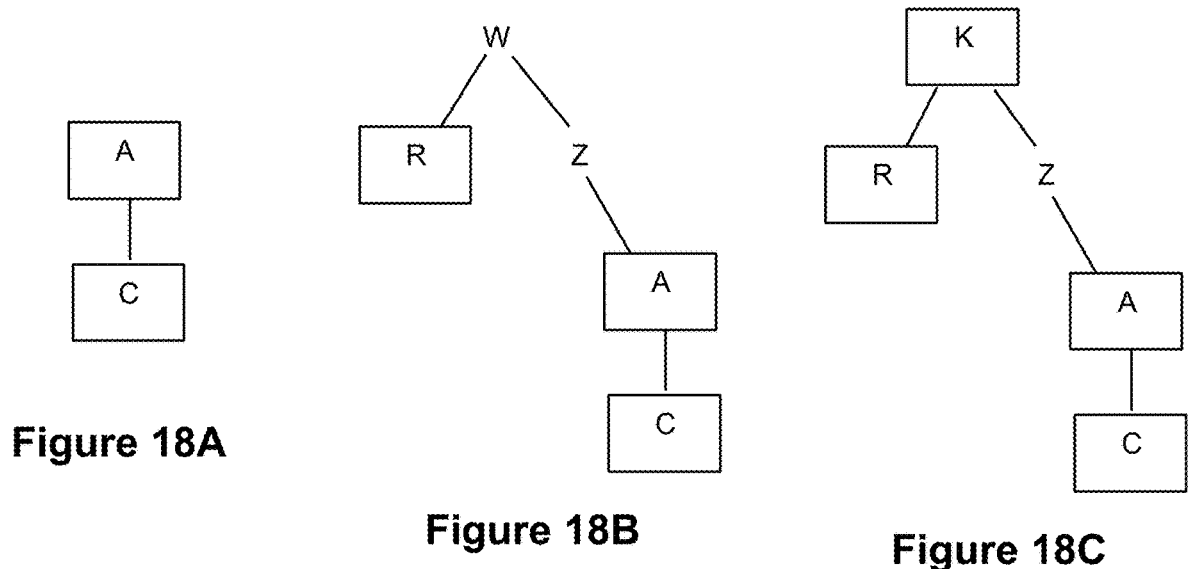
Figure 18A
Figure 18B
Figure 18C
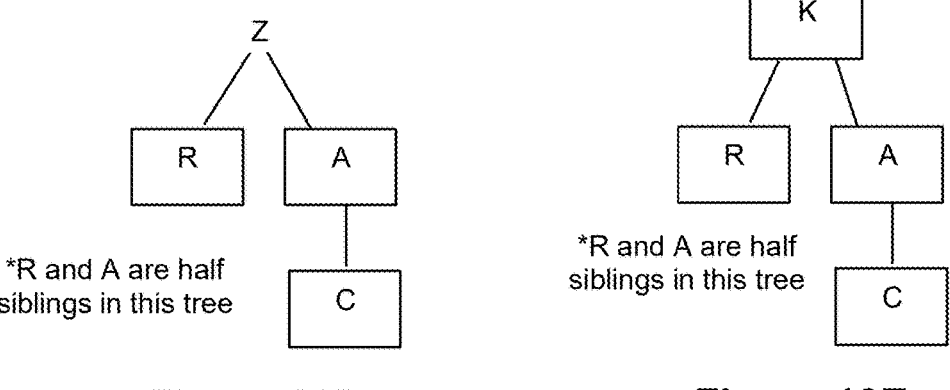
Figure 18D
Figure 18E

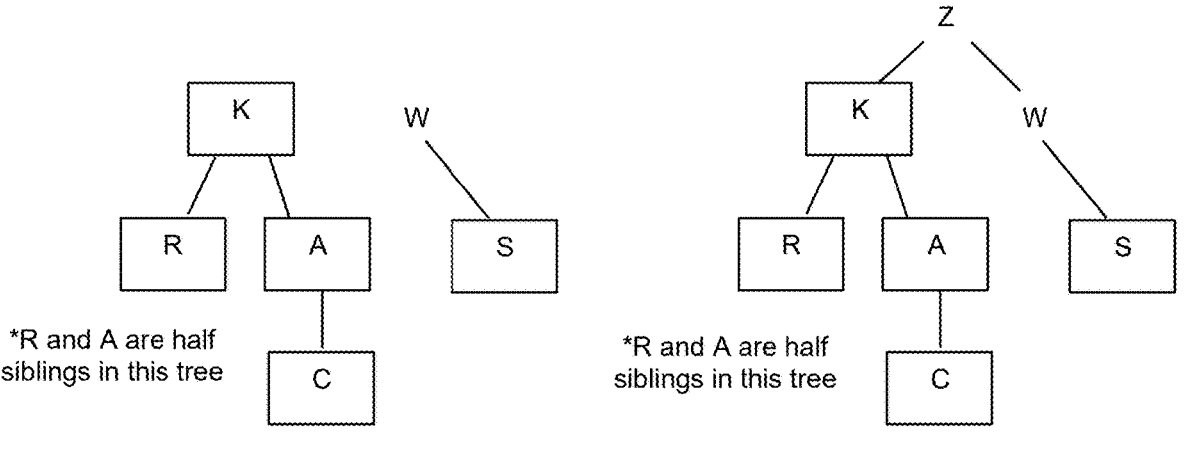
| Figure 19A | Figure 19B |
|:---:|:---:|
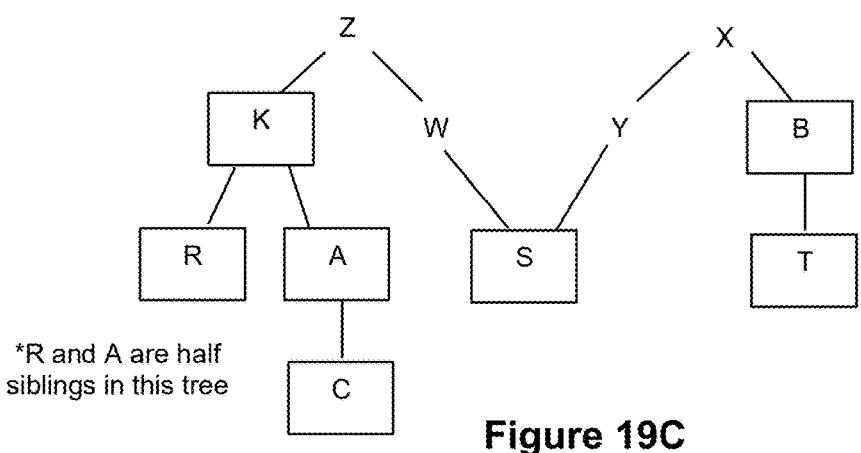
Figure 19C
| Node | Tree Relationship of Node to Primary | Permitted Range of cM Distances for Tree Relationship | cM Distance (Node to Primary) | Does cM Distance Fit Tree Relationship? |
|---|---|---|---|---|
| K | Aunt/Uncle | 1350-2175 | 1705 | Yes |
| R | First Cousin | 550-1225 | 870 | Yes |
| A | Half First Cousin | 135-855 | 450 | Yes |
| C | Half First Cousin, Once Removed | 55-530 | 225 | Yes |
| B | Aunt/Uncle | 1350-2175 | 1695 | Yes |
| T | First Cousin | 550-1225 | 875 | Yes |
Figure 20

APPLIED COMPUTER TECHNOLOGY FOR AUTONOMOUS AND RECURSIVE CLUSTER-BASED GENETIC FAMILY TREE CONSTRUCTION BASED ON MEASURES OF GENETIC RELATEDNESS AMONG INDIVIDUALS

CROSS-REFERENCE AND PRIORITY CLAIM TO RELATED PATENT APPLICATIONS

This patent application claims priority to U.S. provisional patent application 63/387,042, filed Dec. 12, 2022, and entitled "Applied Computer Technology for Autonomous and Recursive Genetic Family Tree Construction Based on Measures of Genetic Relatedness Among Individuals", the entire disclosure of which is incorporated herein by reference.

This patent application also claims priority to U.S. provisional patent application 63/432,623, filed Dec. 14, 2022, and entitled "Applied Artificial Intelligence for Estimating Measures of Genetic Relatedness Between Individuals Based on Non-Genetic Data About Individuals", the entire disclosure of which is incorporated herein by reference.

This patent application is related to (1) U.S. patent application Ser. No. 18/535,559, filed this same day, and entitled "Applied Computer Technology for Autonomous and Recursive Genetic Family Tree Construction Based on Measures of Genetic Relatedness Among Individuals" and (2) U.S. patent application Ser. No. 18/535,630, filed this same day, and entitled "Applied Computer Technology for Autonomous Translation of Measures of Genetic Relatedness Between Individuals into a Tree Structure with Array for Efficient Computer Processing", the entire disclosures of each of which are incorporated herein by reference.

INTRODUCTION

There are tremendous technical challenges in the art for designing computer technology so that it is capable of automating a process of generating a genetic family tree for a target individual based on genetic data about the target individual.

Conventional computer systems in the art for generating such genetic family trees typically rely on measures of genetic relatedness between the target individual and a plurality of other individuals (e.g., centimorgan (cM) distances between the target individual and the other individuals). However, these conventional computer systems suffer from a requirement that extensive user interaction based on trial and error is needed to position the individuals in the genetic family tree for the individual. For example, a conventional approach to family tree building proposes possible genetic relationships between a target individual and other individuals based on known cM distances between the target individual and those other individuals. But, this conventional approach relies on human interpretation and decision-making with respect to how to assemble these individuals into a genetic family tree for the target individual. Accordingly, these conventional systems are at best a graphic version of a simplified statistics table that attempts to propose how the target individual may be related to other individuals while relying on human trial and error to attempt formation of larger genetic family trees.

As a technical improvement in this art, the inventors disclose techniques by which genetic family tree formation is further aided by measures of genetic relatedness between sets of individuals. That is, when building a genetic family tree that links a set of individuals with a target individual, the techniques described herein leverage not only measures of genetic relatedness for the individuals relative to the target individual but also leverage measures of genetic relatedness for the individuals relative to each other.

By using these measures of genetic relatedness between individuals in combination with measures of genetic relatedness for the individuals relative to the target individual, the technology described herein is able to operate more efficiently by limiting how many permutations of potential family trees need to be formed and evaluated during a recursive family tree building process. Moreover, the systematic approach to family tree generation described herein can eliminate human interpretation bias while also providing an ability to shield users from exposure to personally identifiable information about individuals if desired by a practitioner.

Furthermore, the inventors disclose techniques for using such measures of genetic relatedness to group individuals into clusters, deconstruct these clusters into trees of nodes corresponding to the individuals, and recursively build family trees based on the trees of these nodes. Through these techniques, computer systems can generate plausible family trees for target individuals in a highly computationally-efficient manner.

Thus, the inventors disclose improved computer systems that practically apply the technology described herein to yield improved computer systems that are able to do what conventional computer systems have been unable to do using techniques that cannot practically be performed by the human mind. In doing so, these improved computer systems are capable of autonomously resolving family trees that conventional solutions in the art have been unable to autonomously resolve.

Toward these ends, the inventors disclose a method for autonomously translating measures of genetic relatedness between a plurality of individuals into a genetic family tree that includes the individuals, the method comprising (1) autonomously forming a plurality of candidate genetic family trees for a target individual among the individuals based on first data and second data, wherein the first data comprises measures of genetic relatedness for a plurality of the individuals relative to the target individual, and wherein the second data comprises measures of genetic relatedness between a plurality of the individuals; and (2) autonomously scoring the candidate genetic family trees based on the first and second data, wherein the scoring indicates likelihoods that the candidate genetic family trees are correct; and wherein the method steps are performed by one or more processors. The inventors further disclose corresponding computer systems and articles of manufacture for carrying out this method.

The inventors also disclose a method for forming one or more genetic family trees that connect a plurality of individuals based on measures of genetic relatedness between a plurality of the individuals, the method comprising: (1) grouping a plurality of the individuals into a cluster, wherein the cluster comprises only those of the individuals who are (i) are genetically related to a target individual according to first data and (ii) genetically related to each other according to second data, wherein the first data comprises measures of genetic relatedness for a plurality of the individuals relative to the target individual, and wherein the second data comprises measures of genetic relatedness between a plurality of the individuals; (2) deconstructing the cluster into a tree structure based on the first data, wherein the tree structure comprises a plurality of nodes arranged hierarchically, wherein each node corresponds to an individual among the individuals from the cluster; (3) iteratively forming one or more genetic family trees based on pairs of adjacent nodes from the tree structure until the nodes from the tree structure are positioned in the one or more genetic family trees based on the second data as applicable to the individuals corresponding to the pairs of adjacent nodes from the tree structure; and (4) connecting the target individual to the one or more genetic family trees based on the first data; and wherein the method steps are performed by one or more processors. The inventors further disclose corresponding computer systems and articles of manufacture for carrying out this method.

The inventors also disclose a method for translating a plurality of measures of genetic relatedness between a plurality of individuals into a tree structure from which a plausibility of candidate genetic family trees for the individuals can be evaluated, the method comprising: (1) accessing genetic relatedness data for a plurality of individuals, wherein the accessed genetic relatedness data comprises (i) first data that comprises a plurality of measures of genetic relatedness for a plurality of the individuals relative to a target individual and (ii) second data that comprises a plurality of measures of genetic relatedness for a plurality of the individuals relative to each other; (2) forming a tree structure based on the accessed genetic relatedness data, wherein the tree structure comprises a plurality of nodes, wherein the nodes correspond to a plurality of different individuals from the accessed genetic relatedness data who are (i) genetically related to the target individual according to the first data with respect to reference data that defines criteria for relatedness with respect to the measures of genetic relatedness and (ii) genetically related to each other according to the second data with respect to the reference data, wherein the nodes are hierarchically arranged in the tree structure as a function of degree of genetic relatedness according to the measures of genetic relatedness for the nodes' corresponding individuals relative to the target individual, and (3) for each of a plurality of the nodes, (i) determining an array of possible genetic relationships for that node's corresponding individual relative to the corresponding individual of an adjacent node in the tree structure according to the second data with respect to the reference data and (ii) associating that node with its determined array of possible genetic relationships, and wherein the method steps are performed by one or more processors. The inventors further disclose corresponding computer systems and articles of manufacture for carrying out this method. Through this translation, the genetic relatedness data that is stored in computer memory as isolated data values gets converted to a structured format through the tree structure. With this tree structure, the nodes of the tree structure correspond to different individuals found in the genetic relatedness data are associated with arrays of possible genetic relationships between their corresponding individuals and individuals who correspond to adjacent nodes in the tree structure. This structured representation of the genetic relatedness data makes such data significantly more amenable to computerized processing due to the arrays of possible genetic relationships that can be efficiently used by computer algorithms, which may include parallelized computer algorithms, to evaluate the plausibility of different candidate genetic family trees that can be created from the tree structure. In other words, this technical improvement in how genetic relatedness data is represented within computer memory leads to significant improvements in how a computer functions to create genetic family trees from different values of genetic relatedness data pertaining to individuals because the arrays are amenable to parallel, iterative and/or recursive processing by computer algorithms.

These and other features and advantages of the invention will be described in greater detail below.

BRIEF DESCRIPTION OF THE DRAWINGS

FIG. 2 depicts an example process flow for autonomous family tree generation in accordance with an example embodiment.

FIG. 3A depicts an example set of measures of genetic relatedness for individuals relative to a target.

FIG. 3B depicts an example set of measures of genetic relatedness between individuals.

FIG. 3C depicts an example tree structure of nodes that can be generated as a result of cluster deconstruction in accordance with an example embodiment.

FIG. 3D depicts an example node for the tree structure of FIG. 3C.

FIG. 3E depicts an example process flow for determining possible genetic relationships between individuals on the basis of measures of genetic relatedness between the individuals.

FIG. 3F depicts example reference data that defined expected ranges for measures of genetic relatedness with respect to various genetic relationships.

FIG. 10 depicts an example process flow for connecting a family tree to a target in accordance with an example embodiment.

FIG. 12 shows an example set of individuals for family tree construction.

FIG. 13 shows an example set of cM distance values relative to a target for the individuals of FIG. 12.

FIG. 14 shows an example set of cM distance values between the individuals of FIG. 12.

FIG. 15 shows an example set of major clusters produced by the FIG. 4A process flow for the individuals of FIGS. 12-14.

FIGS. 18A-18E show a progression of building candidate family trees for one of the clusters of FIG. 15 by the process flow of FIG. 4B.

FIGS. 19A-19C show a progression of connecting candidate family trees to a target using the process flow of FIG. 10.

FIG. 20 depicts an example table showing how various tree relationships in a family tree can be tested for accuracy.

DETAILED DESCRIPTION OF EXAMPLE EMBODIMENTS

Figure 1:
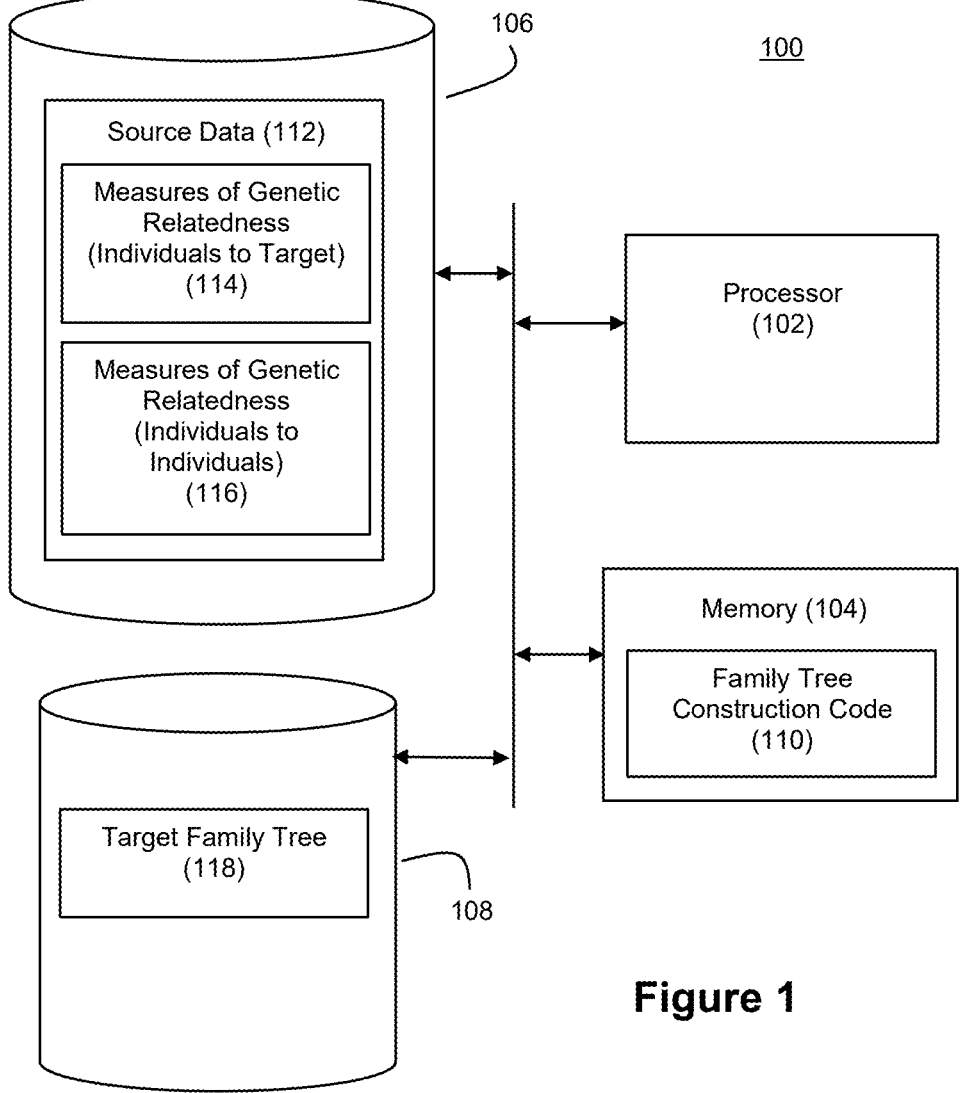
FIG. 1 depicts an example computer system for autonomously generating family trees in accordance with an example embodiment.

FIG. 1 shows an example computer system 100 that can be used to implement autonomous and recursive construction of a genetic family tree of a target individual (the "target") based on measures of genetic relatedness among individuals. For ease of reference, the terms "family tree" and "genetic family tree" will be used interchangeably herein.

The system 100 comprises a processor 102 and associated memory 104 for cooperation with each other to execute family tree construction code 110. For operation, the processor 102 can access a data store 106 in which source data 112 is stored, where source data 112 provides the underlying data for analysis. This source data 112 includes (1) measures of genetic relatedness for individuals relative to the target (see 114) and (2) measures of genetic relatedness among various individuals who may be members of the family tree (see 116). As an example, the measures of genetic relatedness can be genetic distance values such as centiMorgan (cM) distance values. However, it should be understood that other measures of genetic relatedness could be used if desired by a practitioner. For example, the measures of genetic relatedness could take the form of heritable physical features of individuals such as combined landmark similarities between individuals of heritable facial features. In this regard, the measures could, for example, comprise vectors that represent heritable facial traits. Moreover, it should also be understood that the source data 112 may include additional information about individuals, such as names, ages, dates of birth, dates of death, places of birth, places of death, addresses, and/or names or other identifying information for spouses if available or applicable. Moreover, it should be understood that the measures 114 and 116 can take the form of measured genetic distance values, estimated genetic distance values, and/or combinations of measured and estimated genetic distance values if desired by a practitioner.

Processor 102 can remotely access the source data 112 over a network connection if desired. For example, source data 112 may reside on the computer system a first person or organization, while processor 102 and memory 104 may reside on a different computer system (such as a computer system of a second person or organization). However, this need not be the case. For example, the processor 102 may directly access data store 106 via a shared communication bus if desired. Thus, the processor 102, memory 104, and source data 112 can all be resident on a single computer system if desired by a practitioner. Moreover, it should be understood that data store 106 need not be a single data store 106. Data store 106 may comprise multiple data stores in which source data 112 is distributively stored.

The results from execution of code 110 can take the form of data that represents the target family tree (see 118), and the target family tree 118 can be stored in data store 108. Processor 102 can access data store 108 directly (e.g., over a shared communication bus) or remotely via a network connection. Furthermore, the data store 108 may comprise multiple data stores 108 in which target family tree data 118 is stored if desired by a practitioner.

Processor 102 and memory 104 can be part of one or more servers or other computer(s) capable of interacting with other systems as described herein. Computer system 100 may include or interact with any type of communication network, wired and/or wireless, including but not limited to wide area networks such as the Internet or local area networks (e.g., an office intranet). Further still, it should be understood that computer system 100 may also include one or more user computer(s) (not shown) which can include screens on which user interfaces are displayed, where processor 102 can populate these user interfaces with visual representations of the family tree data 118.

The processor 102 can take the form of one or more processors such as CPUs or other compute resources suitable for carrying out the processing operations described herein. For example, in some embodiments, a single processor 102 may be used to carry out the processing operations described herein. As another example, different processors 102 may be used to carry out different ones of the processing operations described herein. Moreover, in example embodiments, the processor 102 may comprise compute resources capable of performing operations in parallel such as processors with multiple processing cores as well as field programmable gate arrays (FPGAs) and/or application-specific integrated circuits (ASICs) with configurable hardware logic capable of operating in parallel. For example, processing operations described herein for building family trees using different indexes of possible genetic relationships among individuals can be deployed on parallel computational resources so that the computer system can generate such family trees concurrently to further accelerate the tree formation process.

Memory 104 can take the form of one or more memory devices, and it can store the code 110 for execution by processor 102 or other data structures for use by processor 102 during operation. Examples of memory 104 that can be used include random access memory (RAM), disk drive(s), or other suitable data storage devices. Moreover, memory 104 can be local to or remote from processor 102.

The family tree construction code 110 can be embodied by machine-readable code that is resident on a non-transitory machine-readable storage medium such as memory 104. The code can take the form of software and/or firmware that define the processing operations discussed herein for execution by the processor 102. The code 110 can be structured in any of a number of different manners, such as in one or more applications or modules for execution by processor 102. For example, a practitioner may employ different applications or modules for operations described herein.

FIG. 2 shows an example process flow for the family tree construction code 110 to be executed by processor 102 in accordance with an example embodiment. This process flow operates on the source data 112. The source data 112 may comprises measures 114 and 116 for a large number of individuals. The source data 112 may arise from any of a number of sources, such as data service providers who can provide genetic information about individuals, public records if available, and/or home-grown data collections from individuals.

At step 200, the processor 102 identifies the target for whom the family tree is to be constructed. The processor 102 can perform step 200 in response to user input that identifies the subject target. Once the target is identified, measures 114 and 116 can be accessed to support the processing operations described herein.

FIGS. 3A and 3B show examples of the measures 114 and 116 that can be used by code 110.

Measures 114 can take the form of a table, matrix, or other data structure where multiple individuals 300 have associated values 302 for measures of genetic relatedness to the target. As noted, in an example embodiment, the values 302 for measures of genetic relatedness can take the form of cM values. For example, Individual 1 can have a value 302 of $x_1$ cM, which indicates the number of centiMorgans between Individual 1 and the target, Individual 2 can have a value 302 of $x_2$ cM, which indicates the number of centiMorgans between Individual 2 and the target, and so on.

Measures 116 can take the form of a table, matrix, or other data structure where multiple individuals 300 have associated values 304 for measures of genetic relatedness between each other. As noted, in an example embodiment, the values 304 for measures of genetic relatedness can take the form of cM values. For example, Individuals 1 and 2 can have a value 304 of $y_{1,2}$ cM, which indicates the number of centiMorgans between Individual 1 and Individual 2, Individuals 1 and 3 can have a value 304 of $y_{1,3}$ cM, which indicates the number of centiMorgans between Individual 1 and Individual 3, and so on. It should be understood that measures 116 may be sparse in that values 304 may not be available for many pairs of individuals 300. In this circumstance, the system can populate the table, matrix, or other data structure with zero or small cM values 304 that would trigger a conclusion of no genetic relationship so that these pairs of individuals can effectively be skipped over during processing operations described herein. As described herein, the code 110 can use measures 116 to improve the efficiency by which the code 110 considers the plausibility and probable viability of various family trees structures for the target that are under consideration. For example, the code 110 can use measures 116 to constrain the number of possible family tree structures that it considers when attempting to organize individuals 300 into a plausible family tree for the target as well as determine the probability that a given plausible family tree corresponds to the true family tree for the target.

At step 202, the processor 102 groups individuals 300 into clusters based on the measures of genetic relatedness for individuals relative to the target (114) and the measures of genetic relatedness between individuals (116) so that each cluster comprises (1) individuals genetically related to the identified target and (2) individuals genetically related to each other. Thus, where the target is the child of two parents (and where such parents are represented as individuals 300 in the source data 112), these two parents would be grouped into separate clusters because while both parents are genetically related to the target, they are not genetically related to each other. Additional clusters can be formed from similar splits elsewhere in the family tree for the target (e.g., the maternal grandfather and maternal grandmother would be included in different clusters because they are not genetically related to each other). As part of the clustering operations of step 202, it should be understood that conclusions about whether individuals 300 are deemed genetically related to the target and to each other can be based on the values 302 and 304. For example, a minimum cM threshold can be defined that would govern whether individuals are deemed genetically related to the target or to each other.

At step 204, the processor 102 deconstructs the clusters formed at step 202 into tree structures. The tree structures can include one or more nodes, where the nodes represent corresponding individuals from the clusters so that each tree structure comprises nodes that are hierarchically arranged based on measures of genetic relatedness for their corresponding individuals to the identified target.

FIG. 3C shows an example tree structure 340 that can be generated by step 204. Tree structure 340 includes a root node 350 and multiple nodes 352 sharing a branch of the tree structure 340, where these nodes 352 correspond to different individuals from a common cluster. As shown by FIG. 3D, each node 352 may comprise an identifier 360 for the node's corresponding individual 300 and an array 362 of possible genetic relationships {R1, R2, . . . , Rm} for the individual 300 of the subject node (node i) relative to node i−1 in the tree structure 340. Examples of possible genetic relationships include parent, child, sibling, half sibling, grandparent, grandchild, aunt/uncle, etc. (see FIG. 3F for an example abbreviated list of possible genetic relationships). The value of m (and thus the number of possible genetic relationships for a given node 352 relative to the next node 352 in the tree structure 340) may vary from node to node. For example, for some nodes, the value of m may be 1 (in which case a given node i has only one possible genetic relationship with node i−1. However, for other nodes, the value of m may be much larger. This array 362 helps constrain the number of family tree permutations that the code 110 needs to consider when evaluating possible family tree structures for the target. Furthermore, as explained above, these arrays 362 in the tree structure 340 are highly amenable to parallelized, iterative, and/or recursive processing to allow the code 110 to efficiently evaluate the plausibility of various candidate genetic family trees that are derived from different permutations of the possible genetic relationships indexed by the arrays 362.

FIG. 3E shows an example process flow that can be implemented by the code 110 to determine the possible genetic relationships that will populate the arrays 362 of the nodes 352.

At step 370, the processor 102 identifies the individual 300 applicable to a subject node 352 (Individual j). This can be determined on the basis of identifier 360 for the subject node 352.

At step 372, the processor 102 identifies the individual 300 for the next node 352 in the tree structure 340 (Individual k). This next node can be the next higher node 352 in the tree structure 340 (in that the next higher node is closer to the root node 350); although it should be understood that the traversal of the tree structure 340 described herein could alternatively travel in the opposite direction if desired by a practitioner, in which case the next node could be the next lower node 352 in the tree structure (in that the next lower node is further from the root node 350).

At step 374, the processor 102 accesses the value 304 for the measure of genetic relatedness between Individuals j and k (Measure jk). This can be accomplished by performing a lookup in the data structure for measures 116 as exemplified by FIG. 3B.

At step 376, the processor 102 determines the possible genetic relationships that exist between Individuals j and k based on Measure jk and reference data that identifies corresponding genetic relationships for different measure values. FIG. 3F shows an example of such reference data 380, where reference data 380 can take the form of a table, matrix, or other data structure that identifies different genetic relationships to a reference individual. Each relationship can have a corresponding range of expected measure values (e.g., a cM distance range) as well as some aggregated value (e.g., an average) that indicates a likely measure value (e.g., an average cM distance) for the subject genetic relationship. At step 376, the processor 102 can perform a lookup in the reference data 380 to find all genetic relationships whose cM distance range encompasses the value for Measure jk for the subject node 352. The processor 102 can then populate the array 362 for the subject node 352 with these possible genetic relationships. Furthermore, a practitioner may find it desirable to populate the array 362 with these genetic relationships in a sort order where the strongest possible genetic relationship will appear first in the array 362 through descending magnitudes of strength to the weakest possible genetic relationship. The strength of a possible genetic relationship for a subject node can be indicated by Measure jk as compared to the aggregated value (e.g., average cM distance for the genetic relationships) or some other formulation for weighing the possible cM values exhibits by the possible genetic relationships.

The example of FIG. 3F shows only a subset of possible genetic relationships, and a person skilled in the art would readily understand that a large variety of additional genetic relationships can be included as part of the reference data 380 (e.g., a "great-great grandparent" relationship, a "half great aunt/uncle" relationship, a "great aunt/uncle" relationship, a "first cousin twice removed" relationship, etc.). Furthermore, it should be understood that the values shown in FIG. 3F are exemplary only, and there are a number of sources available in the art for quantifying measures of genetic relatedness such as cM distances to different genetic relationships. Moreover, a practitioner may choose to employ reference data 380 that varies by geography or other criteria. For example, studies sometimes show that there may be variations in the mappings of genetic relationships to cM distances across geographic regions (e.g., where large metropolitan areas with a long history of highly diverse populations may show lower cM distances for extended relations as compared to geographic regions with small and highly insular populations). Accordingly, the code 110 may also take criteria such as geographic area into consideration when choosing the reference data 380 to use for determining possible genetic relationships at step 376.

While FIG. 3C shows an example where the tree structure 340 includes a single branch of nodes 352 connected to the root node 350, it should be understood that tree structure 340 could include multiple branches of nodes 352 connected to the root node 350. For example, a single tree structure 340 can be formed from the different clusters produced at step 202, and each branch of nodes 352 emanating from the root node 350 can correspond to a different one of these clusters. Alternatively, a practitioner could employ a different tree structure 340 for each cluster from step 202.

Returning to FIG. 2, at step 206, the processor 102 recursively processes the tree structure(s) 340 to build the family tree for the identified target from the individuals included in the nodes 352 of the tree structure(s) 340. This recursive processing can evaluate candidate family trees by building out possible family trees for the individuals 300 corresponding to groups of nodes 352 in the tree structure(s) 340 using the measures 114 and 116 to make decisions about how to link such possible family trees to the identified target, about which candidate family trees are plausible, and about which of the plausible family trees are most likely correct. Probability values can be assigned to plausible family trees to indicate a likelihood that a plausible family tree is correct; and these probability values can be used by processor 102 to make decisions about which family trees can be presented to a user in data store 108.

Figure 4A:
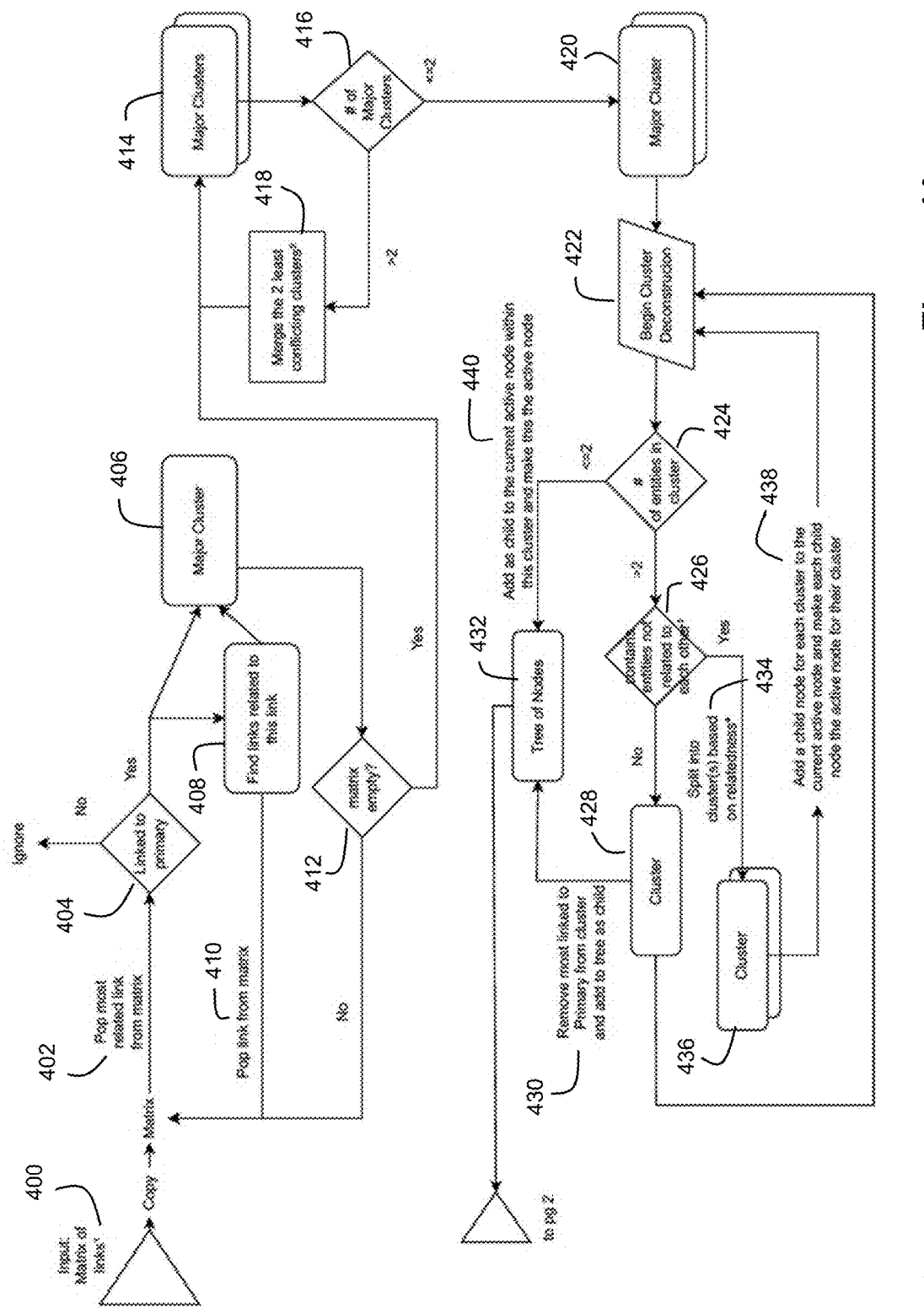
FIG. 4A depicts an example process flow for constructing clusters from individuals and a target and deconstructing the clusters into a tree structure according to an example embodiment.

FIG. 4A shows an example process flow for carrying out steps 202 and 204 of FIG. 2.

Figure 5:
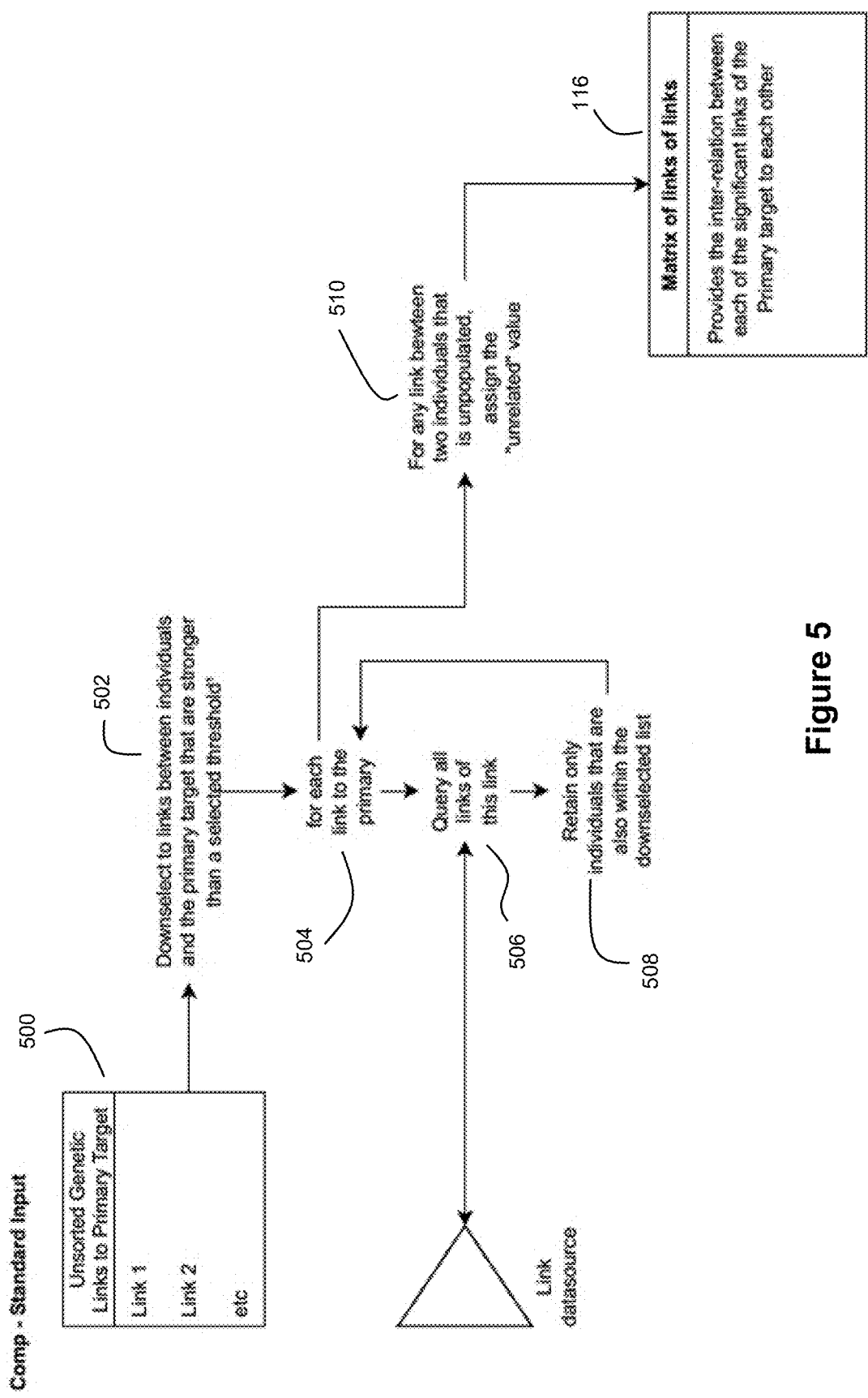
FIG. 5 depicts an example process for generating input data matrices according to an example embodiment.

The FIG. 4A process flow begins by the processor 102 generating input data 400 that can take the form of a matrix of measures 114 and 116. The individuals 300 that populate this matrix can be referred to as links (or individuals 300). FIG. 5 shows an example process flow that illustrates how the input matrix 400 is created.

The FIG. 5 process flow can start with a set 500 of unsorted individuals who have genetic links to the identified target (referenced as the "primary target" or "primary" in the nomenclature of FIG. 5). This set 500 can be accessed from source data 112 via measures 114. At step 502, the processor 102 processes the set 500 to downselect the set 500 to those individuals 300 whose genetic links (as reflected by the cM distances 302 for those individuals 300) to the primary target are greater than a defined threshold. This threshold can be a default threshold defined by a practitioner as a minimum cM distance value between individuals for those individuals to be considered genetically related for purposes of the processing operations described herein. As an example, this threshold could be 12.5 cM. However, it should be understood that practitioners may choose to employ different threshold values. For example, in relatively insular populations with above average endogamy (and therefore larger segments of shared genetic material within the community at large), a practitioner may find it desirable to use a larger threshold value to define unrelatedness.

This downselected set can serve as the measures 114 which comprise the list of individuals 300 who are deemed to be genetically related to the primary target (along with their corresponding cM distances relative the primary target). For each of these individuals 300 (see 504), the processor 102 can query the measures 116 in source data 112 to identify the individuals 300 who are genetically related to the subject individuals 300 as reflected by measures 114 (see step 506). This can also be accomplished by finding the individuals 300 whose cM distances 304 relative to the subject individuals 300 from the measures 114 are greater than the defined threshold that establishes the minimum cM distance for two individuals to be deemed genetically related. At step 508, the processor 102 retains only those individuals 300 from the measures 116 who are also present in measures 114. At this point, the system has a matrix of individuals 300 as reflected by FIGS. 3A and 3B for measures 114 and 116 for linkage to the primary target. To the extent there are pairs of individuals 300 in the matrix of measures 116 (see FIG. 3B) whose cM distance values 304 are unpopulated, the processor 102 can assign a dummy cM value (e.g., a zero value or some other value that is sufficiently small so that the pair of individuals 300 are deemed genetically unrelated to each other) to those pairs of individuals 300 in measures 116.

FIGS. 12-14 show a simple example of how the FIG. 5 process flow can operate to produce measures 114 and 116 for use in the input data matrix 400. FIG. 12 shows an example where S is the primary target, and Individuals K, B, T, R, A, and C are the individuals who exhibit measures 114 that indicate a genetic relationship with S. FIG. 13 shows the measure values 302 for these individuals 300 in connection with this example. By querying the source data 112, the matrix 116 shown by FIG. 14 can be built where several pairs of these individuals have cM distance values between each other that are known. In the example of FIG. 14, the "---" notation indicates that measure values 304 are not available for such pairs of individuals, in which case these pairs of individuals can be linked to zero values or some arbitrary cM value that is sufficiently small for the subject pair of individuals to be deemed genetically unrelated (e.g., 12.5 cM).

Returning to FIG. 4A, the input data 400 can comprise the measures 114 and 116 produced by the FIG. 5 process flow. At steps 402 and 404, the processor 102 finds the individual 300 (referenced as a "link" in the nomenclature of FIG. 4A) who is the most genetically related to the primary target. This determination can be made on the basis of the individual 300 in measures 114 whose cM distance value 302 is the largest. This individual 300 is popped from the input data matrix 400 and placed in a major cluster 406. Also, at step 408, the processor 102 finds all individuals 300 who are genetically related to the individual 300 identified at steps 402 and 404. The individuals 300 identified at step 408 are also popped from the input data matrix 400 (see 410) and placed in the major cluster 406. It should be understood that while typically the individuals 300 identified at step 410 are also individuals 300 with cM distance values 302 relative to the target; this need not be the case. There may be individuals 300 in the source data 112 who have cM distance values 304 indicating they are related to each other, but with no known relationship to the target (e.g., a missing cM value 302 relative to the target).

At this point, the processor 102 checks whether the input data matrix 400 has any individuals left within it (step 412). If yes, the process flow returns to steps 402-404 and the remaining individuals 300 in the input data matrix 400 are checked to see which individual has the largest cM value relative to the primary target. This individual is placed in a new major cluster 406 along with the remaining individuals 300 in the input data matrix 400 who are deemed to be genetically related to this individual 300 (see 408 and 410).

Step 412 then operates to repeat the flow of steps 402, 404, 408, and 410 to create additional major clusters 406 (see 414) until the input data matrix 400 is emptied of individuals. However, it should be understood that there may be cases where only a single cluster is formed as a result of steps 402, 404, 408, and 410 (for example, if the source data 112 includes only one side of the target's family tree, in which case the system 100 can still generate a family tree for the target, albeit one that includes only maternal or paternal genetic ancestors).

Returning to the running example of FIGS. 12-14, for a first iteration of steps 402 and 404, the processor 102 can pop K from the input data matrix 400 because K has the largest cM value relative to S. Furthermore, steps 408 and 410 can operate to also pop R, A, and C from the input data matrix 400 because these individuals are shown by the measures 116 of FIG. 14 to be related to K. This results in the formation of a first major cluster 1500 that comprises K, R, A, and C (see FIG. 15). During a next iteration of steps 402 and 404, the processor 102 can pop B from the input data matrix 400 because B has the largest cM value relative to S of the remaining individuals in the input data matrix 400. Steps 408 and 410 can then operate to also pop T from the input data matrix 400 because T is shown by the measures

116 of FIG. 14 to be related to B. This results in the formation of a second major cluster 1502 that comprises B and T (see FIG. 15).

While the examples of FIGS. 12-15 show a simple case where steps 402, 404, 408, 410, and 412 operate to sort the individuals 300 into two clusters 414, there may be instances where the operation of these steps produces more than two clusters 414. This scenario can arise in circumstances such as those where the source data 112 includes distant relatives and/or the source data 112 includes incomplete samples. As an example, suppose the only results on the maternal side came from two people who were half second cousins to each other. These half second cousins could have a cM distance below the relatedness threshold (e.g., 12.5 cM), and the initial clustering would not realize that they both should actually be in the same major cluster on the maternal side. For an example of incomplete samples, consider two aunts on the maternal side who both sought genetic testing; but they used two different genetic services. If the system 100 had access to both of these services but not the underlying genetic data, and the target was in both services, then the system 100 would know that these two females had a very close genetic relationship to the target but the system 100 would not see any genetic relationship between the two of them (in which case they may land in separate major clusters 414).

In the scenario where there are more than two clusters 414, steps 416 and 418 operate to merge clusters in a fashion that produces two major clusters 420. In a typical case, these two major clusters 420 would generally correspond to a first major cluster 420 comprising the individuals 300 who are maternally related to the primary target and a second major cluster 420 comprising the individuals 300 who are paternally related to the primary target; although other cluster relationships to the target could arise. To support these cluster merging operations, step 416 operates to check whether the number of clusters 414 is greater than 2. If no, these clusters 414 can then serve as the major clusters 420. If yes, step 418 operates to merge the two least conflicting clusters of the clusters 414. Steps 416 and 418 can then be repeated until the number of remaining clusters has been reduced to two major clusters 420.

Figure 6:
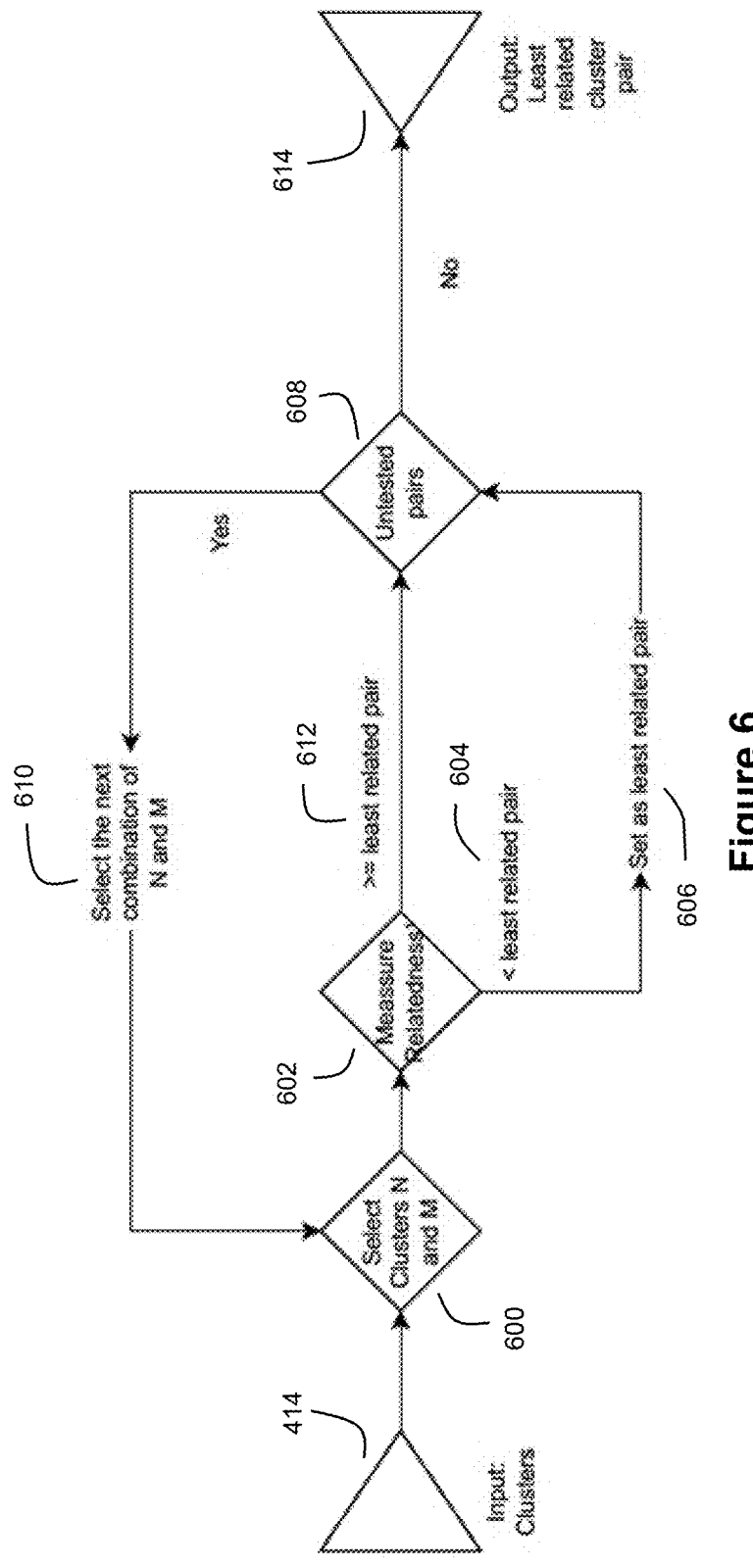
FIG. 6 depicts an example process flow for identifying least conflicting clusters according to defined criteria in accordance with an example embodiment.

FIG. 6 shows an example process for carrying out step 418. The FIG. 6 process flow begins with a set of 3 or more clusters 414. At step 600, the processor 102 selects two of these clusters (Clusters N and M). At step 602, the processor measures the genetic relatedness of Clusters N and M. In an example embodiment, step 602 can operate to identify the pair of individuals 300 who are in different ones of the Clusters N and M and who are the most genetically related to each other (as indicated by the largest cM value 304 as between the subject pair of individuals 300) relative to the other permutations of pairs of individuals in Clusters N and M. However, it should be understood that the relatedness of clusters can be measured in different manners if desired by a practitioner. For example, the system can find pairs of individuals 300 who are in different ones of Clusters N and M and who are genetically related to each other, and the system could then average the top specific number of pairs (while assuming an "unrelated' value for each missing pair when the desired number of specific pairs exceeds the actual number of pairs); in which case this average value could serve as an indicator of cluster relatedness.

Figure 7:
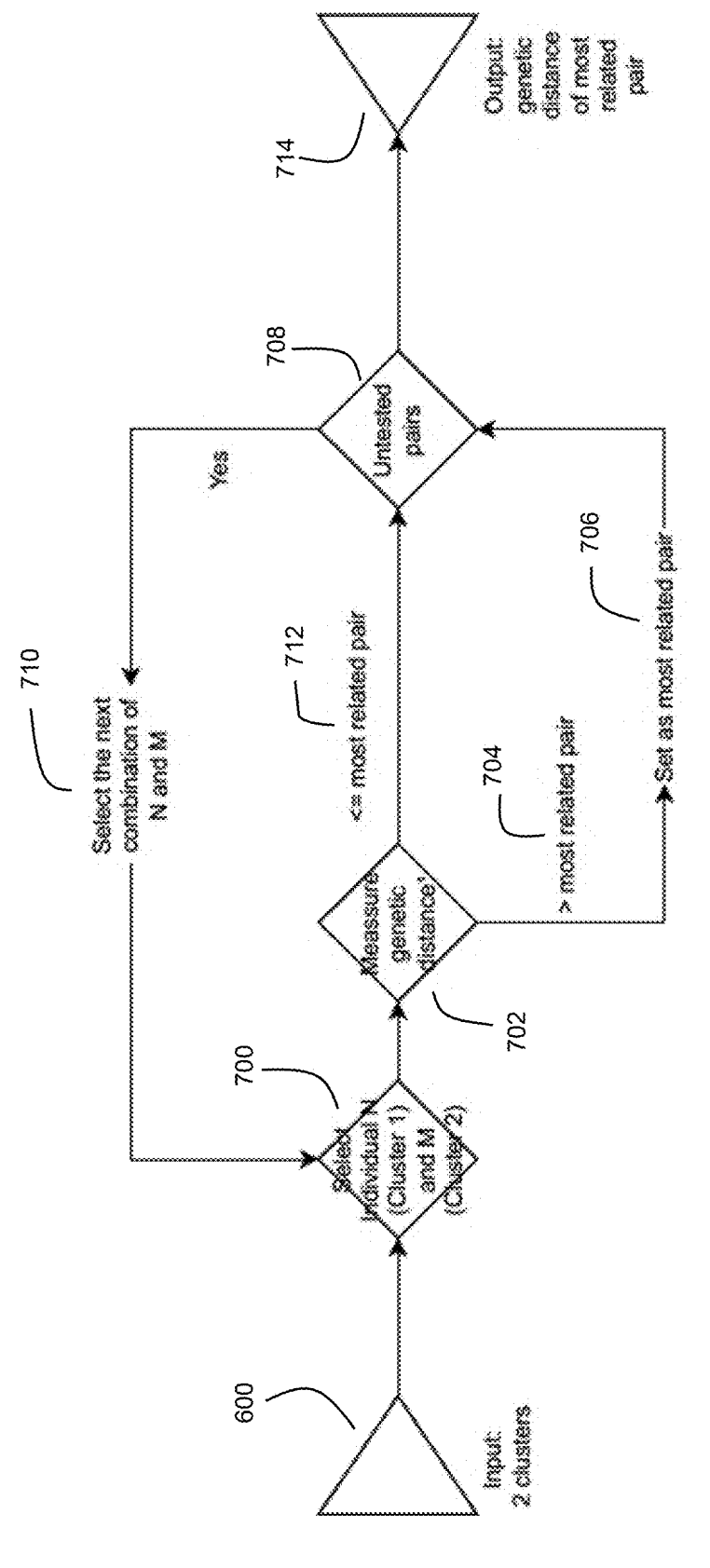
FIG. 7 depicts an example process flow for measuring the relatedness of clusters according to defined criteria in accordance with an example embodiment.

FIG. 7 shows an example process flow for how step 602 can be carried out. FIG. 7 starts with the two Clusters N and M. At step 700, the processor 102 selects Individual N (from Cluster N) and Individual M (from Cluster M) (where the N and M for Individuals N and M are index values that support traversing all permutation of pairs of individuals 300 across the different Clusters N and M). At step 702, the processor 102 determines the genetic distance between Individuals N and M. With this example, the genetic distance can be determined on the basis of the cM value 304 for Individuals N and M from measures 116. The processor 102 then tests this determined genetic distance to determine whether Individuals N and M are the most related pair of individuals tested thus far for Clusters N and M (see step 704). If yes, this pair of individuals is set as the most related pair (step 706). On a first pass through steps 702 and 704, it should be understood that these two Individuals N and M will be set as the most related pair.

At step 708, the processor 102 determines whether there are any more pairs of individuals across the two Clusters N and M who have not yet been tested for relatedness. If any untested pairs remain, the processor 102 selects the next permutation of pairs of Individuals N and M (see 710) and returns to steps 700 and 702 where the genetic distance between this next pair of individuals is measured. The measured genetic distance of the next individual pair can be compared with the current "most related pair" to determine which cM value is larger (and thus indicate more genetic relatedness). If the new individual pair has a larger cM value than the current "most related" pair, then steps 704 and 706 operate to make this new individual pair the "most related pair". But, if the new individual pair does not have a larger cM value than the current "most related" pair, then step 712 operates to effectively discard the new individual pair and return to step 708. It should be understood that the FIG. 7 process flow effectively operates to find the pair of individuals in different Clusters N and M who are the most genetically related as indicated by their cM value 304, where the cM value 304 for the most related pair of individuals from Clusters N and M can then serve as a proxy value for the relatedness of Clusters N and M that is determined by step 604.

Returning to FIG. 6, at steps 604 and 612, the processor 102 can compare the measured relatedness for Clusters N and M with the measured relatedness for the pair of clusters currently determined to be the "least related". If the measured relatedness for current Clusters N and M is less than the relatedness of the cluster pair that had previously qualified as "least related" (see 604), then step 606 can set the current pair of Clusters N and M as the least related cluster pair. It should be understood that on a first pass through the FIG. 6 process flow, Clusters N and M will by default be set as the least related cluster pair.

At step 608, the processor 102 determines whether there are any more pairs of clusters that have not yet been tested for relatedness. If any untested cluster pairs remain, the processor 102 selects the next permutation of pairs of Clusters N and M (see 610) and returns to steps 600 and 602 where the relatedness of this next pair of clusters is measured. The measured relatedness of the next cluster pair can be compared with the current "least related pair" to determine which cM value is smaller (and thus indicate less genetic relatedness). If the new cluster pair has a smaller cM value than the current "least related" cluster pair, then steps 604 and 606 operate to make this new cluster pair the "least related pair". But, if the new cluster pair does not have a smaller cM value than the current "least related" pair, then step 612 operates to effectively discard the new cluster pair and return to step 608. It should be understood that the FIG. 6 process flow effectively operates to find the pair of clusters that are deemed to be the least genetically related as indicated by the cM values 304 of each cluster pair's most related pair of inter-cluster individuals. This least related cluster pair can then be identified (step 614) and merged to form a single cluster that comprises the individuals 300 from the two clusters of the least related cluster pair.

Returning to FIG. 4A, the system now has two major clusters 420, and a cluster deconstruction process begins at step 422. The cluster deconstruction process operates to convert the two major clusters 420 into one or more tree structures 340 (see "tree of nodes" 432 shown by FIG. 4A).

The cluster deconstruction process can begin with one of the major clusters 420 and then repeat itself with respect to the other major cluster 420.

At step 424, the processor determines how many individuals 300 are present in the subject cluster 420. If the number of individuals 300 is less than or equal to 2, then this pair of individuals 300 can be added to the tree structure 340 as a pair of nodes 352. If step 424 concludes that the number of individuals 300 in the subject cluster 420 is less than or equal to 2 during a first pass of step 424, then this pair of nodes 352 can be connected to the root node 350 for the tree structure 340 that serves as the tree of nodes 432 (step 440). Otherwise, step 440 would connect this pair of nodes 352 to the most recently added node 352 on the tree 432.

If step 424 results in a determination that more than 2 individuals 300 are present in the subject cluster 420, then the process flow proceeds to step 426. At step 426, the processor 102 determines whether the subject cluster 420 includes any individuals 300 who are not genetically related to each other. This determination can be made on the basis of the cM values 304 as between all pairs of individuals 300 who are present in the subject cluster 420.

If step 426 results in a determination that the subject cluster 420 includes only individuals 300 who are genetically related to each other, then the process flow can proceed to 428 where this subject cluster is processed and the individual 300 within the subject cluster who is most genetically related to the primary target can be removed from the subject cluster and added as a node 352 to the tree of nodes 432 (see 430). The determination of which individual 300 within the subject cluster is most genetically related to the target (denoted as "Primary" in FIG. 4A) can be made on the basis of which individual 300 has the largest cM value 302 within measures 114 relative to the primary target.

If step 426 results in a determination that the subject cluster 420 includes any individuals 300 who are genetically unrelated to each other, then the process flow can proceed to step 434 where this subject cluster is split into clusters so that the individuals 300 from the subject cluster 420 who are not genetically related to each other start their own clusters 436 (and where these clusters 436 are then populated with the individuals 300 from the subject cluster 420 who are genetically related to the founding member of each subject cluster 436).

Figure 8:
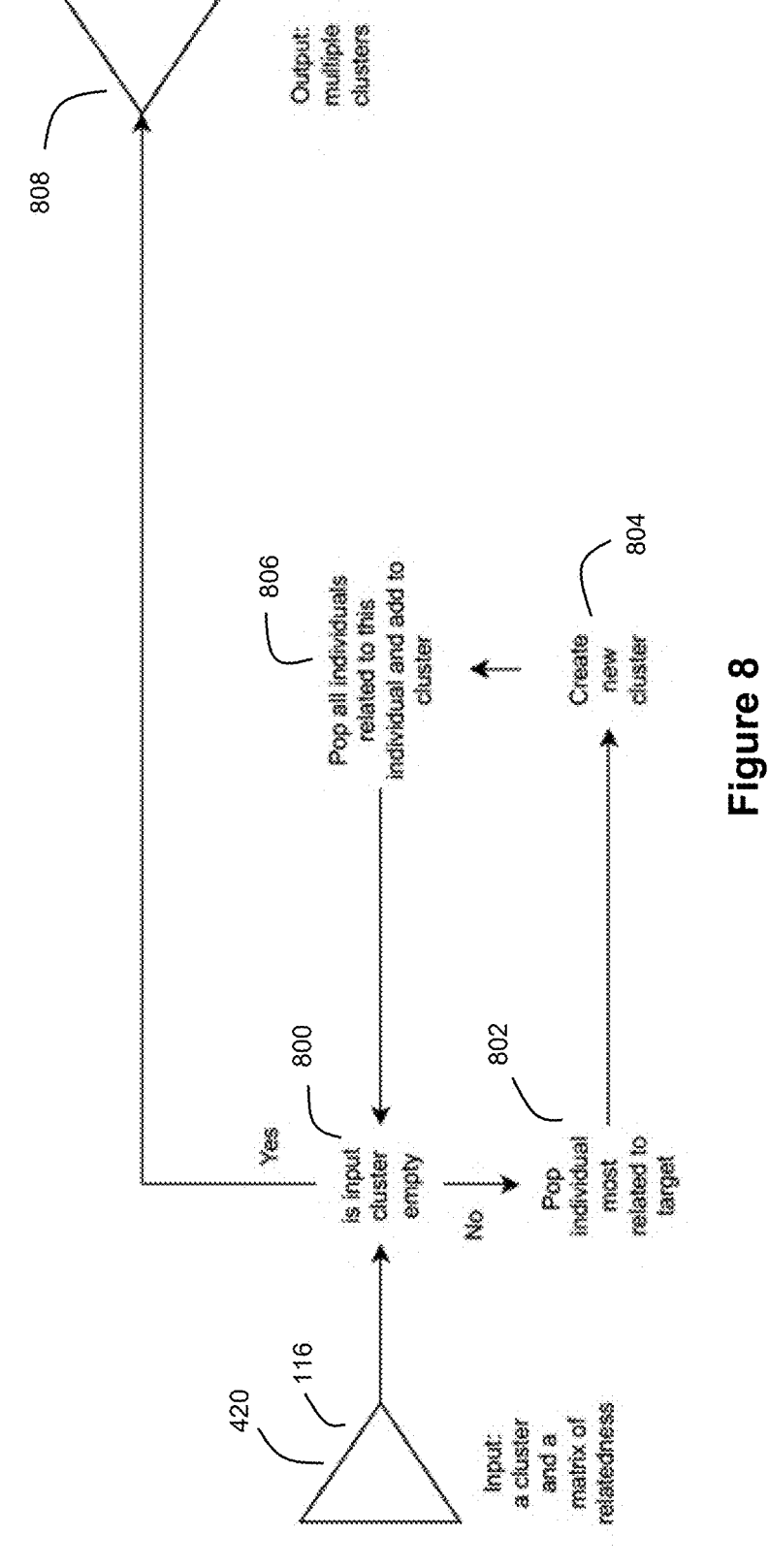
FIG. 8 depicts an example process flow for splitting clusters to separate individuals who are unrelated to each other in accordance with an example embodiment.

FIG. 8 shows an example process flow for how step 434 can be carried out. FIG. 8 can start with a subject cluster 420 and measures 114 and 116 applicable to the individuals 300 who are members of the subject cluster 420. At step 800, the processor 102 checks whether the subject cluster is empty. If not, the process flow proceeds to step 802. At step 802, the processor 102 pops the individual 300 from the subject cluster 420 who is the most genetically related to the primary target (based on the cM values 302 from measures 114 for the individuals 300 who are present in the subject cluster 420. The processor 102 then creates a new cluster 436 using the individual 300 who is most genetically related to the primary target (see step 804). At step 806, the processor 102 determines all remaining individuals 300 who are members of the subject cluster 420 and are genetically related to the individual 300 added to new cluster 436 at step 804 (as determined by the cM values 304 for the individuals 300 in measures 116 who are deemed genetically related to the founding member of the new cluster 436). The process flow then returns to step 800 to determine whether the subject cluster 420 is now empty. If not empty, steps 802, 804, and 806 are repeated (and another new cluster 436 is created). Eventually, the subject cluster 420 will be emptied of individuals 300 and the process flow can proceed to output step 808 where the new clusters 436 are returned.

Steps 426 and 434 can operate in scenarios where the subject major cluster 420 includes unrelated individuals 300 such as spouses who are ancestors of the primary target. For example, two individuals who are married to each other and are maternal or paternal grandparents of the primary target would be genetically related to the primary target but (likely) not genetically related to each other. By splitting these spouses (or other individuals 300 who are genetically related to the primary target but not genetically related to each other) into their own clusters 436, the clustering operations described herein can operate to produce clusters of individuals 300 where each cluster comprises individuals 300 who are (1) genetically related to the primary target and (2) genetically related to each other. These clusters can then serve as the basis for formation of the tree structure(s) 340/432 as described herein. By splitting the clusters based on likely separations between maternal and paternal genetic contributors, the remaining clusters that form the basis of tree structure(s) 340/432 tend to hold the genetically closest relatives. Given that uncertainty regarding the family tree relationships between individuals tends to increase as the genetic closeness between those individuals decreases, the clustering techniques of FIG. 4A help ensure that the portions of the family tree that require the fewest assumed intervening members and with the lowest assumed error rate will form the foundation of subsequent tree additions. This not only improves computational efficiency and time-to-solution in tree formation, but also yields higher confidence about the resulting tree structures.

Figure 3G:
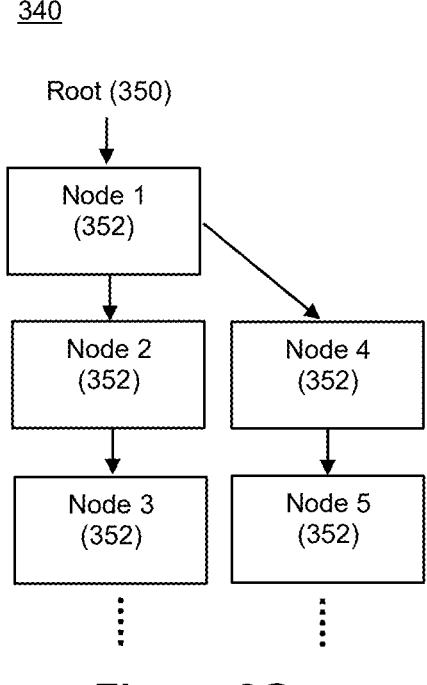
FIG. 3G depicts an example tree structure of nodes with multiple branches corresponding to different clusters.

At step 438, a new child node for each cluster 436 is added to the tree 432, where this child node is connected to the current active node of the tree 432. It should be understood that the current active node of the tree 432 is the node 352 that was most recently added to the tree 432 by the process flow. These newly added child nodes can then serve as the current active node on the tree 432 for their respective clusters 436. FIG. 3G shows an example of a tree structure 340 that can be formed from multiple clusters that get split by relatedness at 434. In the example of FIG. 3G, a split creates two branches off Node 1 (where Nodes 2 and 3 can reside in a first branch of the tree structure 340 and Nodes 3 and 4 can reside in a second branch of the tree structure 340.

From step 438, the process flow returns to step 422 to perform the cluster deconstruction process with respect to the newly formed clusters 436 As part of this, the processor 102 can select one of the new clusters 436 to process for adding nodes 352 to the tree 432. Steps 424, 426, 430, and 440 can then operate on each pass of the process flow to add nodes 352 to the tree 432 in a descending order of relatedness to the primary target until the clusters are fully converted into the tree 432.

Returning to the example of FIGS. 12-15, the two clusters 1500 and 1502 can be processed through cluster deconstruction from step 422 as follows.

For cluster 1500 (with individual members {K, R, A, and C}), step 424 will conclude that the population of cluster 1500 is greater than 2 and proceed to step 426. Given that each of K, R, A, and C are genetically related to each other, the process flow will proceed from step 426 to step 430. At step 430, K (as the individual 300 within cluster 1500 with the largest cM value 302) is removed from cluster 1500 and added to the tree 432 as the first node 352 connected to the root node 350 (see FIG. 16A).

The process flow then returns to step 424, where the node 352 for K serves as the active node of the tree 432. Step 424 once again concludes that the remaining population of cluster 1500 is greater than 2. Given that R, A, and C are genetically related to each other, the process flow proceeds to step 430 where R (as the remaining individual 300 within cluster 1500 with the largest cM value 302) is removed from cluster 1500 and added to the tree 432 as the second node 352 connected to the node 352 for K (see FIG. 16B).

The process flow then returns to step 424 again, where the node 352 for R serves as the active node of the tree 432. On this pass, step 424 results in a conclusion that the remaining population of cluster 1500 is 2. In this case, the process flow proceeds to step 440 and adds A, C as node pair to the tree 432 (where the A-C node pair connects to the node 352 for R (see FIG. 16C). It should be understood that the processor 102 can connect A and C to the tree 432 in a hierarchical manner if desired where A connects to R and where C connects to A based on A having a larger cM value 302 than C. Cluster 1500 will then have been depopulated by the cluster deconstruction process.

Next, the cluster deconstruction process can operate on cluster 1502 (with individual members B and T), and where the active node of the tree 432 returns to the root node 350. Step 424 will result in a conclusion that the population of cluster 1502 is 2; in which case, the process flow proceeds to step 440 and adds B, T as node pair to the tree 432 (where the B-T node pair connects to the root node (see FIG. 16D). As noted above in connection with the pair A and C, it should be understood that the processor 102 can connect B and T to the tree 432 in a hierarchical manner if desired where B connects to R and where T connects to B based on B having a larger cM value 302 than T. Cluster 1502 will then have been depopulated by the cluster deconstruction process.

Figure 4B:
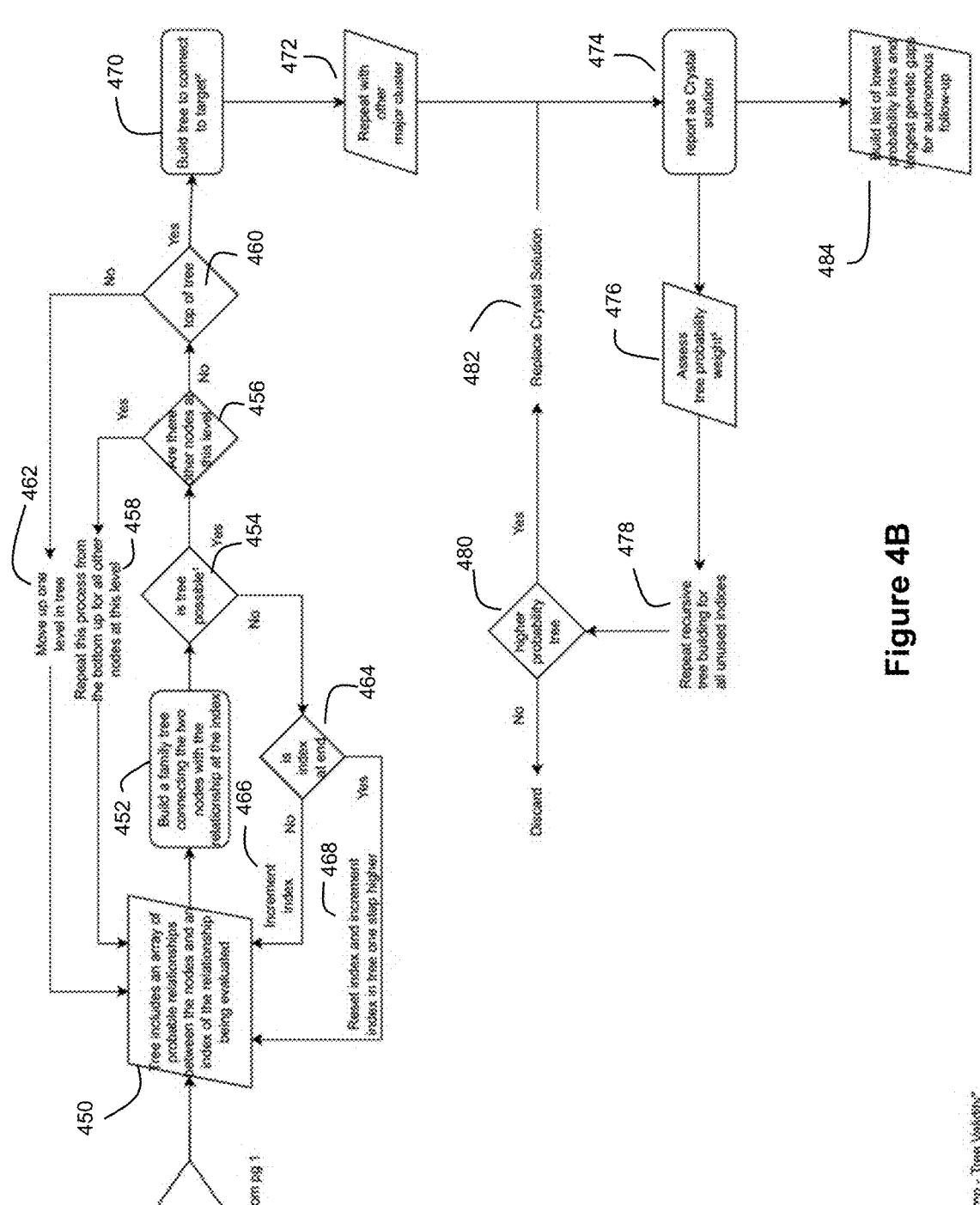
FIG. 4B depicts an example process flow for recursively building and evaluating family trees on the basis of the tree structures produced by FIG. 4A.

Now that the FIG. 4A process flow has created the tree 432, the code 110 can proceed with recursive family tree formation (see step 206 of FIG. 2). FIG. 4B shows an example process flow for carrying out step 206 of FIG. 2.

The FIG. 4B process flow begins by the processor 102 populating the nodes 352 of tree 432 with arrays 362 of possible genetic relationships between adjacent pairs of nodes 352 (see step 450). As noted above, FIG. 3E shows an example process flow for creating such arrays 362. Returning to the example of FIGS. 12-16D, step 450 can augment the tree 432 with arrays 362 as shown by FIG. 17, where FIG. 17 depicts a representation of tree 432 as augmented with arrays 362 for each node 352.

At step 452 of FIG. 4B, the processor 102 builds a candidate family tree that connects the two nodes 352 that are at the bottom of the tree 432. In building this candidate family tree, the processor 102 can maintain two indexes-a tree index that identifies the node 352 of tree 432 that is being worked on and a relationship index that identifies which genetic relationship in the array 362 of the subject node 352 is being considered. The tree index can be initialized to the bottom of tree 432, and the relationship index can be initialized to the first relationship in array 362 for the subject node 352. Thus, at step 452, the processor 102 can select the bottom pair of nodes 352 in the tree 432 and build a family tree that connects the individuals 300 for these nodes using the relationship specified by the relationship from array 362 that is identified by the relationship index. If the relationship between the node pair is not a direct relationship, step 452 may create empty or "dummy" nodes in the candidate family tree that serve as placeholder nodes to suitably connect the nodes in the subject node pair so that they exhibit the specified relationship from the array 362. For example, if the specified relationship for the node pair X-Y is an aunt/uncle relationship, the processor 102 can generate a parent of Node X, a grandparent of Node X (through the parent), a sibling of the parent (where the grandparent is the parent of the sibling), and include Node Y as the child of the sibling of the parent (to thereby create a sufficient family tree for establishing that Node Y is an aunt or uncle to Node X).

Figures 16A, 16B, 16C, 16D, 17:
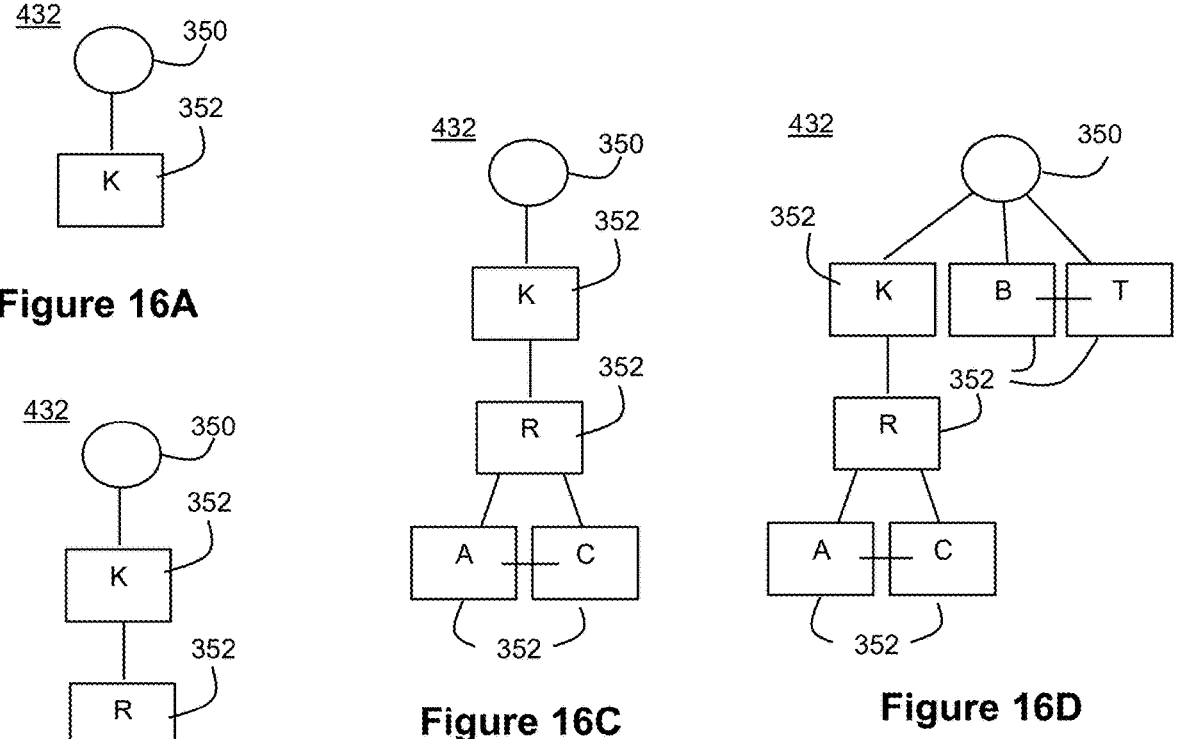
FIGS. 16A-16D shows an example progression of building a tree structure of nodes corresponding to the individuals of FIGS. 12-15 by the FIG. 4A process flow.
FIG. 17 shows another representation of the tree structure of FIG. 16D including an array of possible genetic relationships between next nodes higher in the tree.

Returning to the example of FIGS. 12-17, step 452 can operate on the tree 432 shown by FIG. 17 to first select the node pair A and C (where C is the bottom node in the tree and A is the next node up). The array 362 for A can be initialized to the parent relationship, and step 452 can create a candidate family tree where A is the parent to C (see FIG. 18A).

The process flow can then proceed to step 454 where the candidate family tree is tested for validity. At step 454, the processor 102 can check the measures 116 for the known members of the candidate family tree as against the other known members of the candidate family tree to see if their cM distance values 304 fall within an acceptable range for the genetic relationships that are defined by the candidate family tree (see FIG. 3F). If any of these cM distance values 304 fall outside the acceptable range of cM values for the specified relationship, then the candidate family tree can be deemed invalid.

Figure 9:
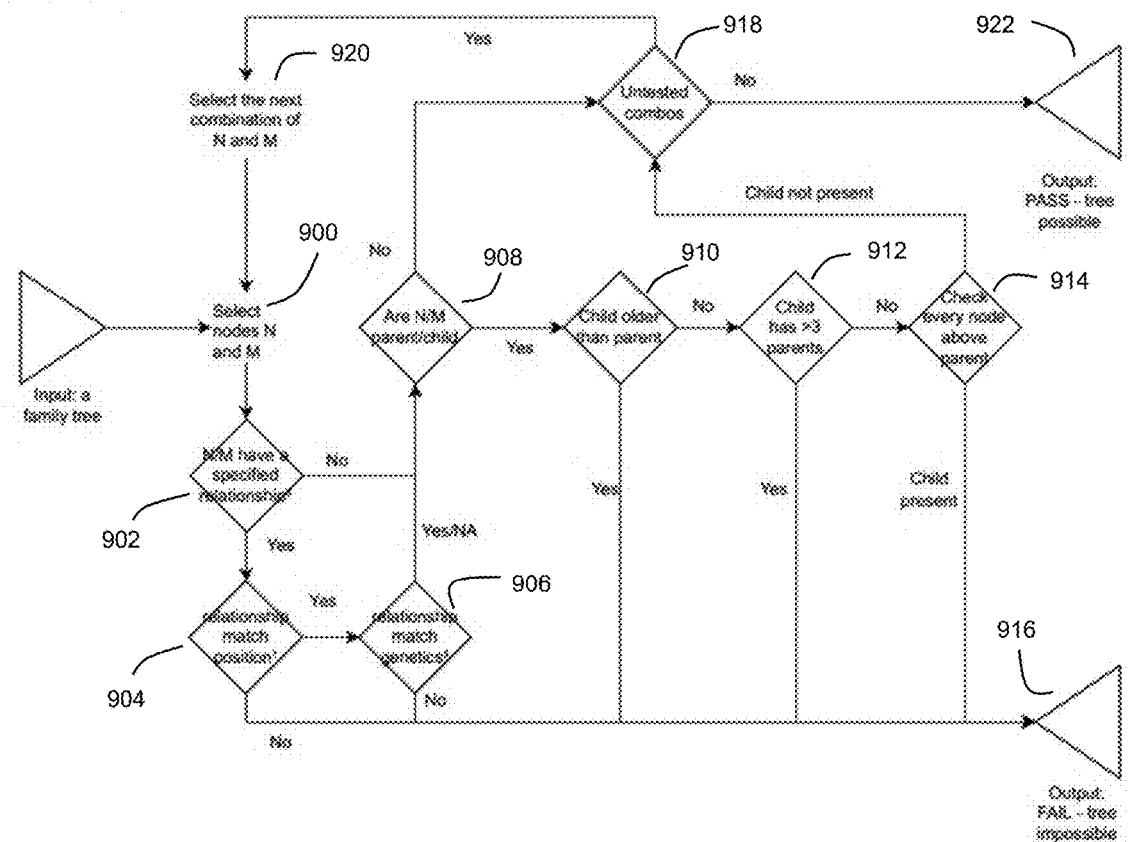
FIG. 9 depicts an example process flow for testing the validity of a candidate family tree in accordance with an example embodiment.

FIG. 9 shows an example process flow for testing family tree validity as part of step 454. With FIG. 9, the input is a candidate family tree that comprises at least two nodes with a specified relationship between each other.

At step 900, the processor 102 selects Nodes N and M in the input candidate family tree. At step 902, the processor 102 checks whether there is a specified relationship between Nodes N and M that is available in the source data 112 and based on information different than the relationship from array 362. For example, source data 112 may include metadata about the pair of individuals 300 corresponding to Nodes N and M that identify these individuals as parent/child according to a birth certificate or other resource. As another example, there may be a DNA test result that may specify a particular relationship between these individuals. If step 900 results in a determination that there is such a specified relationship for the individuals corresponding to Nodes N and M, then the processor 102 can check whether this specified relationship matches the position of the individuals on the candidate family tree. If not, the candidate family tree can be deemed invalid and discarded (see 916).

But if the pair of individuals for Nodes N and M pass step 904 (or if step 902 results in a determination that there is no need for the secondary specified relationship check), the process flow can proceed to step 906. At step 906, the processor 102 determines whether the tree's relationship between the individuals corresponding to Nodes N and M fit the measure value 304 between those individuals. As noted above, if the cM distance value 304 between the individuals 300 corresponding to Nodes N and M fall within an acceptable range for the genetic relationships that are defined by the candidate family tree (see FIG. 3F), then the process flow can advance to step 908. If this cM distance value 304 falls outside the acceptable range of cM values for the specified relationship, then the candidate family tree can be deemed invalid (see 916).

If the subject nodes pass step 906, the process flow can start performing additional validity checks. At step 908, the process flow checks whether the individuals corresponding to Nodes N and M exhibit a parent/child relationship in the candidate family tree. If not, the process flow proceeds to step 918 where the processor 102 checks for additional untested pairs of individuals in the candidate family tree. It they exist, the next combination of Nodes N and M are selected (step 920) and step 900 is repeated. If step 908 results in a determination that the individuals corresponding to Nodes N and M exhibit a parent/child relationship in the candidate family tree, then the process flow proceeds to steps 910, 912, and 914 where the validity of this parent/child relationship is tested.

At step 910, the processor 102 checks whether age information is available for the pair of individuals under consideration. If so, a check is performed to ensure that the candidate child is younger than the candidate parent (and this testing may also include a requirement that the degree by which the child is younger would correspond to the parent being sufficiently old to be deemed capable of producing a child if desired by a practitioner). If the prospective child is older than the prospective parent, this would result in the candidate family tree being declared invalid (see 916). It should be understood that step 910 may not be performed if the source data 112 for the relevant individuals does not include age information.

At step 912, the processor 102 checks the candidate family tree to see if the candidate child has more than three candidate parents in the candidate family tree. If yes, the candidate family tree can be declared invalid (see 916).

At step 914, the processor 102 checks the candidate family tree to see if the candidate child is also present in the candidate family tree in any nodes above the candidate parent. If yes, the candidate family tree can be declared invalid (see 916).

If the individuals corresponding to Nodes N and M pass all of the tests 910, 912, and 914, the process flow can proceed to step 918 and check for untested combinations of individuals from the candidate family tree. If untested combinations exist, step 920 can be performed and the process flow can repeat. If there not any remaining untested combinations, then the process flow can conclude that the candidate family tree is not thus far invalid (see 922).

If the candidate family tree passes step 454, the process flow will continue to step 456. At step 456, the processor 102 checks whether there are additional nodes in the tree 432 at the same level as the current tree index. If yes, the process flow returns to 450 and step 452 is performed for the other node(s) at the same tree index level in tree 432. If step 456 results in a determination that there are not other nodes in the tree 352 at the same level as the current tree index, then step 460 checks whether the tree index is at the top of the tree 432. If not, the tree index is incremented by 1 (see 462), and the process flow returns to steps 450 and 452. On this return to step 452, the candidate family tree is augmented to add the next node from tree 432 to the candidate family tree using the relationship in the array 362 for the next node as indicated by the relationship index. This augmented family tree can be tested for validity at step 454 as the process flow recurses.

Returning to the example of FIGS. 12-18A, FIG. 18B shows an example of an augmented family tree that can be constructed on a first repeat of step 452. In this iteration, the subject node is R and the specified relationship as between R and A is a relationship where R is the aunt/uncle of A. To accommodate this relationship, a dummy parent (Z) of A can be added to the candidate family tree, a dummy grandparent (W) of A can be added to the candidate family tree (where W is also the parent of Z), and where R is added to the candidate family tree as a child of W. This results in R serving as an aunt/uncle of A. At this point, the candidate family tree would be deemed valid because the cM distance values 304 between R and A, between R and C, and between A and C are all within acceptable boundaries.

Continuing with this example, steps 456, 460, and 462 will operate to return to steps 450 and 452 to next add K to the candidate family tree. The specified relationship from the array 362 for R to K with respect to the current relationship index is a parent relationship. Thus, step 452 can operate to augment the candidate family tree by making K a parent of R. Given that the candidate family tree already has a dummy parent of R (see W in FIG. 18B), step 452 can operate by replacing W with K as shown by FIG. 18C. However, the tree validity testing at step 454 for the candidate family tree of FIG. 18C will fail because this candidate family tree has K serving as the grandparent of A. According to FIG. 3F, the permitted range of cM distances for a grandparent relationship is 1150 cM to 2315 cM. However, FIG. 14 shows that K and A share a CM distance value of 3395 cM, which is too large for a grandparent relationship. This means that the candidate family tree will be found invalid at step 454.

If step 454 results in a determination that the candidate family tree is invalid, then the process flow proceeds to step 464. At step 464, the processor 102 checks whether the relationship index is at the end of the subject array 362. If not, the relationship index is incremented (step 466), and steps 450 and 452 operate to test the subject node pair for the next relationship in the subject array 362. Continuing with the example of FIGS. 12-18C, this would mean that K is added to the candidate family tree of FIG. 18B as a child of R. However, this candidate family tree would also fail at step 454 because the shared cM distance value between K and A is too large for a valid first cousin relationship between K and A. This means that the processor 102 would conclude that R is not an aunt/uncle of A because none of the possible permutations for the K-R relationship will work if R is the aunt/uncle of A. Accordingly, the candidate family tree would need to revert back to the candidate family tree of FIG. 18A.

In operation, the process flow would proceed to step 464 upon the failure of the relationship where K is a child of R, and step 464 would result in a determination that the relationship index is at the end because both of the possible relationships in the array for the K-R relationship had been tested. Accordingly, the process flow would proceed from step 464 to step 468. At step 468, the tree index would return to be pointing at R and the relationship index for R would be incremented to specify the next relationship in the array 362 of possible relationships between R and A. In the example of FIG. 17, it can be seen that the next relationship in the subject array is the half sibling relationship.

Upon the return to steps 450 and 452 from step 468, step 452 will operate to build a candidate family tree as shown by FIG. 18D where R is the half sibling of A. With this construction, there will be a dummy parent (Z) who is the parent of both R and A. This candidate family tree will be validated at step 454, and the process flow will return to step

452 to augment the candidate family tree of FIG. 18D with the next node K where K is added to the family tree as the parent of R (as per the first relationship in the array 362 for the R-K possible relationships). Given that Z already exists in the candidate family tree as a parent of R, step 452 can operate to simply replace Z with K as shown by FIG. 18E. The validation testing of the candidate family tree of FIG. 18E at step 454 will result in a conclusion that this candidate family tree is valid because the K-A relationship is also a parent relationship and the cM distance between K and A as per FIG. 14 (3395 cM) is within the valid range for a parent/child relationship as per FIG. 3F (a range of 3325 cM to 3725 cM).

Once K has been successfully added to the candidate family tree, step 460 will conclude that the processor 102 has reached the top of tree 432 because the next node up from K is the root node 350. As such, the process flow would proceed from step 460 to step 470. At this point, the family tree of FIG. 18E serves as a plausible family tree for cluster 1500 shown by FIG. 15.

At step 470, the processor 102 operates on the candidate family tree to connect it to the primary target. This step can leverage the known measure 114 that expresses the cM distance as between the most recent node added to the candidate family tree (e.g., K in the running example) and the primary target (e.g., S in the running example).

FIG. 10 shows an example process for carrying out step 470. The FIG. 10 process flow operates as a family tree builder based on most recent common ancestor (MRCA) principles. The input to the FIG. 10 process flow are two nodes (individuals) for the candidate family tree and a specified relationship between them. The two nodes that serve as inputs are (1) a node corresponding to the primary target (where this node is to be added to the candidate family tree) and (2) the node corresponding to the subject individual from the candidate family tree built from the subject cluster 420 (e.g., cluster 1500 in the running example) who has the largest measure 302 of relatedness relative to the primary target. For the running example of FIGS. 12-18E, the primary target is S and the subject individual with the largest measure 304 of relatedness to S from cluster 1500 is K (see FIG. 13). The specified relationship would be a possible genetic relationship that exists between the primary target and the subject individual on the basis of measure 302 for the subject individual. As noted above, the possible genetic relationships can be determined on the basis of measure 302 for the subject individual relative to the permitted ranges of relatedness measures for different genetic relationships (see FIG. 3F). It should be understood that it may be possible that multiple possible genetic relationships may exist between the subject individual and the primary target, in which case an array of possible genetic relationships can be determined, and the FIG. 10 process flow can be repeated for each of these possible relationships (e.g., see step 478 discussed below). For the running example of FIGS. 12-18E, K could have any array of possible genetic relationships to S of {Aunt/Uncle, Half Sibling, Niece/ Nephew, Grandparent, Grandchild, Great Aunt/Uncle, Great Niece/Nephew}.

At step 1000, the processor 102 determines whether the subject specified relationship as between the primary target and the subject individual is a parent/child relationship.

If step 1000 results in a determination that the specified relationship is a parent/child relationship, then step 1002 operates to add the primary target to the candidate family tree so that the primary target connects to the node corresponding to the subject individual in accordance with the specified parent/child relationship. At step 1016, this candidate family tree is then output as a candidate family tree with a connection to the primary target.

If step 1000 results in a determination that the specified relationship is not a parent/child relationship, then the process flow proceeds to step 1004. From step 1004, the process flow figures out how the candidate family tree should be filled out with placeholder nodes (where the placeholder (or dummy) nodes correspond to individuals who are not represented by individuals 300 within the source data 112) so that the primary target can be connected to the candidate family tree. At step 1004, the processor 102 determines which of the two nodes under consideration (the primary target and the subject individual) are generationally the youngest according to the specified relationship. The node that is generationally the youngest is set as the "current node", while the other is set as the "target node". For example, with respect to the running example of FIGS. 12-18E, where the process flow is working on a relationship where K is an aunt/uncle of S, the "current node" would be set to be S and the "target node" would be set to K.

At step 1006, the processor 102 checks whether the current node and the target node are in the same generation. If not, at step 1008, a new parent node is added to the candidate family tree This parent node is then set as the "current node" and the process flow returns to step 1006. This looping of steps 1006 and 1008 results in parent nodes being added to the tree until a parent is added who is of the same generation as the target node (taking into consideration the role of the target node according to the input specified relationship).

Once the candidate family tree has a parent node of the same generation as the target node, the process flow proceeds to step 1010. At step 1010, the processor 102 checks whether the recombination distance between the current node and the target node is one (1). All relationships in a family tree can be expressed in terms of (1) a generational distance relative to each other and (2) a recombination distance relative to each other, where the generational and recombination distances effectively serve as a coordinate system for navigating through relationships on the family tree. A table or other data structure can be maintained by the system 100 that identifies the generational distance and recombination distance between all possible nodes on a family tree (or at least a large number of such nodes depending on how large of a family tree the system supports), and the processor 102 can perform lookups in this table or data structure as needed to support the operations of steps 1006 and 1010.

The generational distance between two nodes on a family tree represents how many generations difference exist in the family tree between the two nodes. When two nodes on a family tree are of the same generation (e.g., siblings relative to each other or their cousins), their generational distance will be zero. The generational distance between a child and that child's parent would be 1. Similarly, the generational distance between a child and that child's aunt/uncle would be 1. The generation distance between a parent and that parent's child would be −1.

The recombination distance between two nodes on a family tree represents how many generations of people would need to breed to make the family tree sufficiently wide for fitting the two nodes. Thus, for direct ancestors of a subject person (e.g., parents, grandparents, etc.) and direct descendants of the subject person (e.g., children, grandchildren, etc.) the recombination distance will be zero. For siblings of the subject person, the recombination distance would be 1 because 1 generation of people breeding (the parents of the sibling) would be needed for the family tree be wide enough to accommodate the sibling. For a niece/nephew of the subject person, the recombination distance would also be 1 because once the family tree has the subject person's parent, it is wide enough to accommodate not only the sibling but also the child of the sibling (i.e., niece/nephew). For an aunt/uncle or a cousin of the subject person, the recombination distance would be 2 because the family tree would need both the parents and grandparents of the subject person in order to be wide enough to accommodate the aunt/uncle and the cousin.

In terms of coordinates (recombination distance. generational distance), the coordinates for various relationships can be expressed as the following:

| Relationship (relative to subject person) | (Recombination Distance, Generational Distance) |
|---|---|
| Parent (of subject person) | (0, 1) |
| Child (of subject person) | (0, −1) |
| Sibling (of subject person) | (1, 0) |
| Niece/Nephew (of subject person) | (1, −1) |
| Aunt/Uncle (of subject person) | (2, 1) |
| Cousin (of subject person) | (2, 0) |

For navigating between nodes on a family tree on the basis of this coordinate system, the coordinate system can employ an order of operations for expressing the recombination and generational distances. This order of operations can be to first resolve the recombination distance and then resolve the generational distance. So, for navigating from a subject person to that person's nephew on a family tree would be a recombination distance of 1 and a generational distance of −1 (1,−1). Thus, starting from the person as "self" on the tree, a recombination distance of 1 goes up to the generation of the person's parent. From there, the generational distance would count down 1 from the subject person to arrive at the generation that holds the subject person's nephew.

If step 1010 results in a determination that the recombination distance between the current node and the target node is one, this means that the current node and the target node are siblings (or perhaps half siblings) because step 1010 will only be reached when the generational distance between the current node and the target node is zero. In this situation, the processor 102 adds a parent (shared) to both the current node and the target node (step 1014). From there, the process flow proceeds to step 1016 and outputs the candidate family tree where the primary target has also been connected to the tree in a manner appropriate to the specified input relationship.

If step 1010 results in a determination that the recombination distance between the current node and the target node is not one, this means that the family tree is not yet wide enough to accommodate the specified relationship between the subject individual and the primary target. Accordingly, the process flow will proceed to step 1012 and add different parent nodes to both the current node and the target node before returning to step 1010. These two new parent nodes would then be set as the current node and the target node for the return to step 1010. Eventually, enough parent nodes will be added to the family tree to reduce the recombination distance between the current node and the target node to one, which allows for the candidate family tree to be completed via steps 1014 and 1016.

Returning to the running example of FIGS. 12-18E, the FIG. 10 process flow would operate on the candidate family tree of FIG. 18E where the inputs to the process flow are K and S with a specified relationship of (say) an aunt/uncle relationship so that K is an aunt/uncle to S. In this scenario, the flow would move from step 1000 to step 1004. At step 1004, S would serve as the "current node" and K would serve as the "target node" since K is generationally older than S according to the specified relationship. At step 1006, the system would determine that K and S are not in the same generation, so step 1008 would operate to add a parent node (W) to the current node(S). This would yield a candidate family tree as shown by FIG. 19A. On the return to step 1006, W serves as the current node, and K remains the target node. In this circumstance, W and K are in the same generation so the process flow would progress from step 1006 to step 1010. At step 1010, the recombination distance between W and K is checked. Since W and K are siblings, this means the recombination distance is 1. In this circumstance, the process flow moves from step 1010 to step 1014 and adds a new parent node Z that is the parent of both the current node (Z) and the target node (K), as shown by FIG. 19B. The candidate family tree of FIG. 19B would then be output at step 1016.

Returning to FIG. 4B, the process flow proceeds to step 472 from step 470. At step 472, the processor repeats the recursive tree building process for the nodes on the tree 432 corresponding to the other major cluster 420. Continuing with the running examples of FIGS. 12-19B, this would mean that a candidate family tree is constructed for nodes B and T (see FIGS. 15 and 16D). It should be understood that step 452 would produce a candidate family tree where B is a parent of T. In this circumstance, step 470 would then operate on B and S, where the specified relationship between B and S is a relationship where B is an aunt/uncle of S. Step 470 would then connect S to the candidate family tree that includes B in the same effective manner as S was connected to the candidate family tree that includes K (see FIG. 19C). The candidate family tree of FIG. 19C can then serve as a candidate family tree for the primary target S that includes the individuals 300 in source data 112 that are known to be genetically related to S (as indicated by the cM distance values) along with placeholder nodes that fill in the family tree up through the most recent common ancestor (MRCA).

At step 474, this candidate family tree can be set as the current "best fit" or "solution" family tree for the primary target if it is the most probable family tree produced by the system for the primary target thus far. Accordingly, on a first pass of step 472, it should be understood that the first family tree generated by the system will be deemed the best fit/solution. However, it should be understood that as additional family trees are generated by the FIG. 4B process flow via steps 450-472, one of these other family trees may replace the current family tree as the best fit/solution if so indicated by the data.

Figure 11:
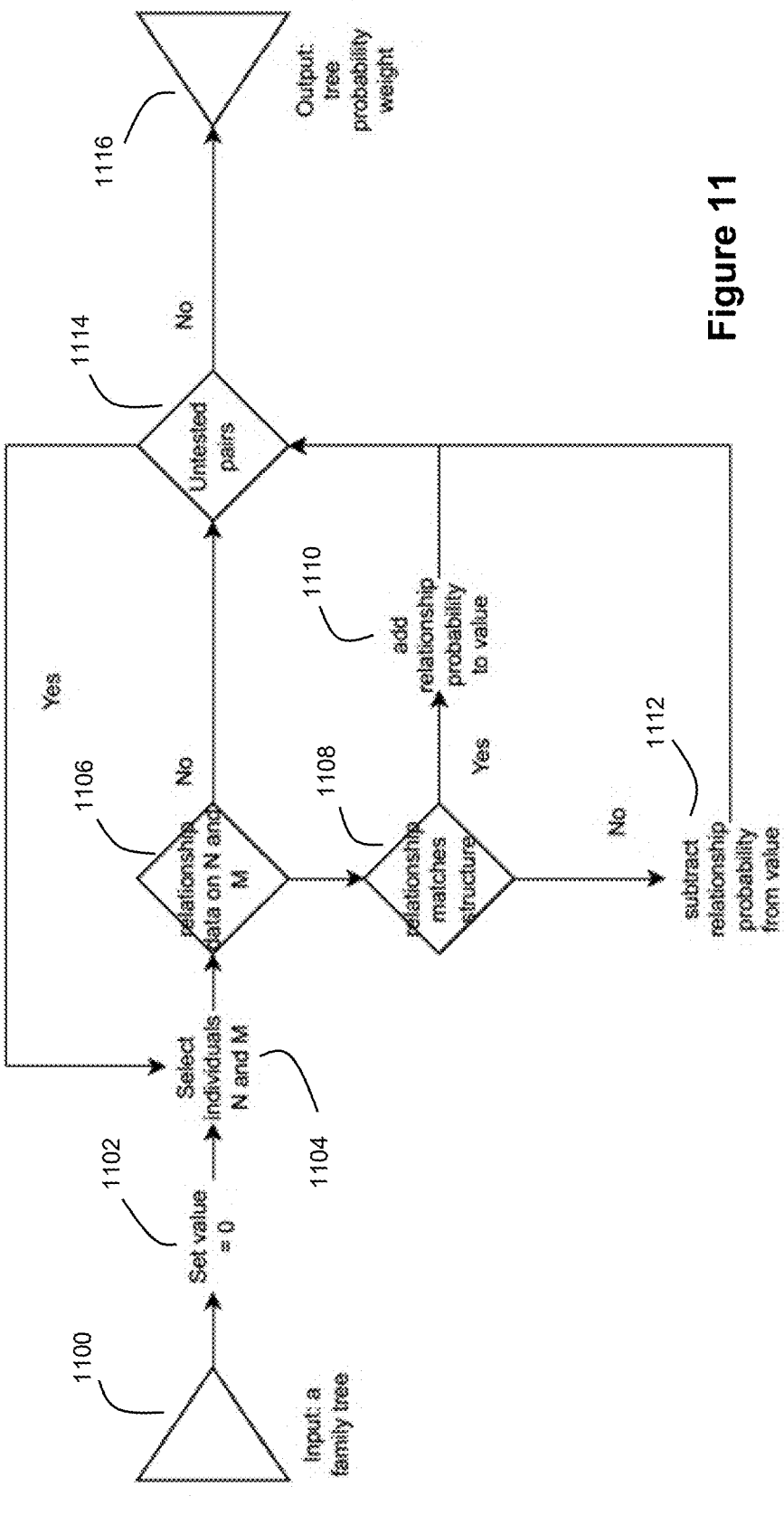
FIG. 11 depicts an example process flow for computing a score for a family tree that indicates a probability that the family tree is correct in accordance with an example embodiment.

Toward this end, step 476 operates to compute a score such as a probability weight for the current family tree that indicates a likelihood that the current family tree is the true family tree for the primary target. FIG. 11 depicts an example process flow for computing a family tree's score (e.g., probability weight) at step 476.

The input 1100 to the FIG. 11 process flow is the family tree output by step 472. At step 1102, the score is initialized to zero. At step 1104, the processor 102 selects a pair of nodes (N and M) from the family tree that correspond to individuals 300 from the source data 112. At step 1106, the processor determines the cM distance value (as derived from 302 or 304 as applicable) for the pair N and M. At step 1108, the processor 102 checks whether this cM distance value fits the relationship between N and M defined by the family tree. If step 1108 results in a determination that the cM distance value between N and M falls within the permitted range of cM distance values for the tree's relationship between N and M, then step 1110 adds a unit of relationship probability to the score. If step 1108 results in a determination that the cM distance value between N and M does not fall within the permitted range of cM distance values for the tree's relationship between N and M, then step 1112 subtracts a unit of relationship probability from the score. For ease of illustration, these units of relationship probability can be a plus/minus "1". However, it should be understood that alternative units of scoring could be employed if desired by a practitioner. For example, the unit of relationship probability can be defined as the area under the probability curve defined by a set interval around the given genetic distance for the subject relationship. Further still, it should be understood that the scoring could be scaled/normalized if desired by a practitioner (such as a score that indicates a percentage of tree relationships that are "correct" on the basis of their cM distance values, rather than a raw accumulated score).

From steps 1110 or 1112, the process flow proceeds to step 1114, where the processor 102 checks for any untested pairs of individuals 300 from the input family tree 1100. In this fashion, the FIG. 11 process flow can cycle through all possible pairs of individuals 300 who are present on the family tree and update the score accordingly. Once all possible pairs have been tested in this fashion, step 1116 can output the score for the subject family tree.

Continuing with the running example of FIG. 12-19C, it should be understood that the individuals who are tested by the FIG. 11 process flow are S, K, R, A, C, B, and T. Furthermore, it should be appreciated from the nature of the tree building process discussed above, that the family tree will exhibit relationships between K and S and between K and B that will be deemed to match the measures 302 for K and B relative to S at step 1108 because the tree building is premised on the validity of those tree relationships. Similarly, the inter-relationships in the family tree among K, R, A, and C as well as the inter-relationships in the family tree among B and T will be deemed to match the measures 304 among these individuals at step 1108 because the tree building is also premised on the validity of those tree relationships. However, there will be several relationships relative to S that are as yet untested in the tree building process. In particular, the following pairs of individuals will have uncertainty as to whether their tree relationship is consistent with their measure 302: (R,S), (A,S), (C,S), and (T,S). FIG. 20 demonstrates these relationships and how they fare at step 1108, where the "tree relationship" of the node to the primary(S) for each individual is expressed in terms of the node/individual's relationship to the primary with respect to the family tree of FIG. 19C (e.g., K is an aunt/uncle of S, R is a first cousin of S, etc.). As can be seen from FIG. 20, the cM distances between (K,S), (R,S), (A,S), (C,S), (B,S), and (T,S) all fit the tree relationship. Accordingly, the family tree of FIG. 19C exhibits a high probability of being correct.

Returning to FIG. 4B, the process flow progresses from step 476 to step 478. At step 478, the processor 102 repeats the recursive tree building process for all unused relationship indices from the steps 450, 452, 470, and 472. It should be understood that this means the process flow may produce a number of different family trees that are passed to step 476. At step 480, the processor 102 decides which of these family trees exhibits the highest score (probability weight). This highest-scoring family tree can be reported as the best fit/solution (step 482). However, it should be understood that the system can maintain a log of all of the family trees that it generates, where each family tree is associated with its computed score.

At step 484, the processor 102 can annotate one or more of the family trees to identify links in those trees that exhibit a probability of correctness below a defined threshold (e.g., links between individuals whose cM distances are located toward the edges of the permitted range of cM distances for the subject tree relationship) and/or identify gaps between known individuals 300 in the family tree that are above a defined threshold (e.g., how many dummy nodes are added to the family tree to fill in gaps between known individuals 300 from the source data 112). These annotations can be reported to user or other applications for follow-up.

In this fashion, FIGS. 4A and 4B illustrate example process flows by which computer system 100 can autonomously generate family trees 118 relative to primary targets based on measures 114 and 116 within source data 112.

While the invention has been described above in relation to its example embodiments, various modifications may be made thereto that still fall within the invention's scope.

Figure 21:
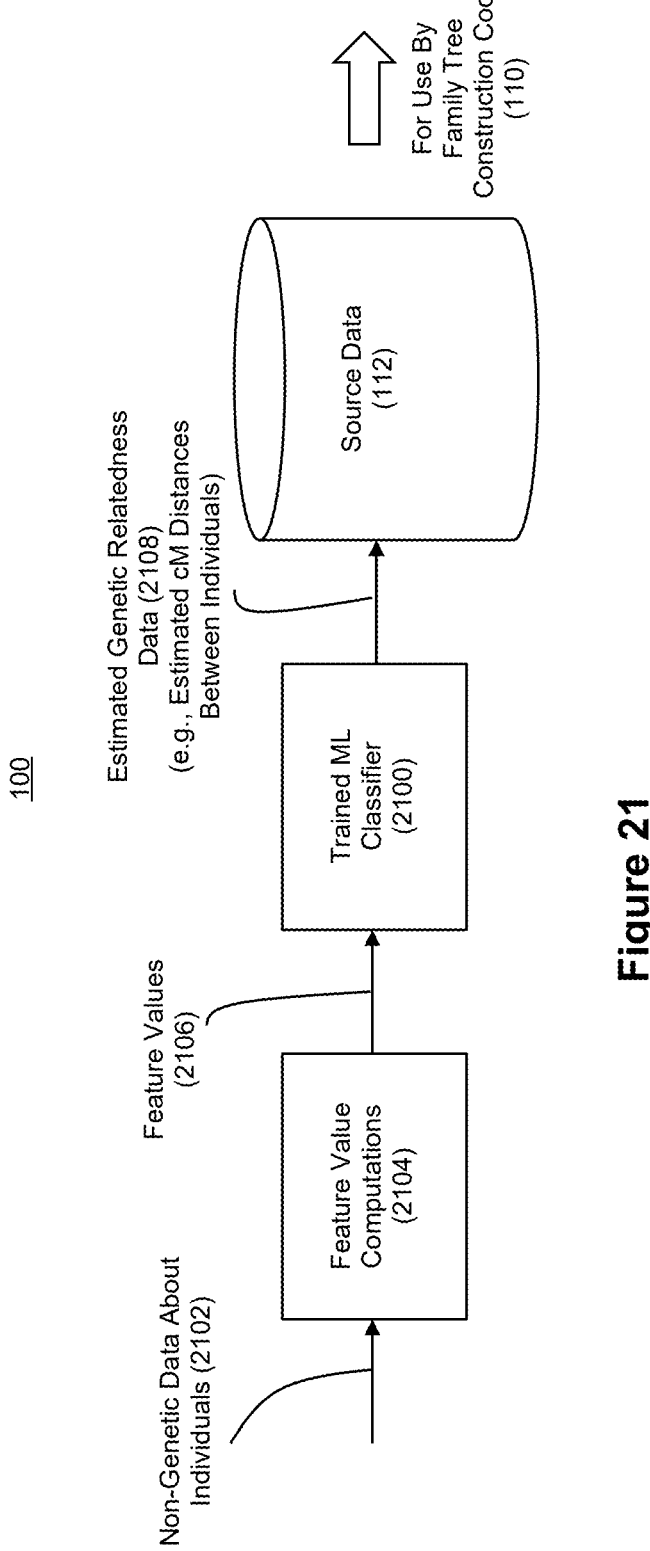
FIG. 21 depicts an example computer system that generates estimated measures of genetic relatedness for use in autonomously generating family trees in accordance with an example embodiment.

For example, as noted above, one or more of the measures of genetic relatedness within measures 114 and/or 116 may comprise estimated measures of genetic relatedness such as estimated cM distances for use as measures 114 and/or 116 for one or more individuals. The above-referenced and incorporated U.S. provisional patent application 63/432,623, filed Dec. 14, 2022, and entitled "Applied Artificial Intelligence for Estimating Measures of Genetic Relatedness Between Individuals Based on Non-Genetic Data About Individuals" describes various techniques whereby machine learning (ML) can be used to train an ML classifier to estimate measures of genetic relatedness between individuals based on non-genetic information about the individuals. The trained ML classifier can then operate on like types of non-genetic data about individuals to predict their measures of genetic relatedness to each other. These estimated measures of genetic relatedness can be included within the source data 112, in which case the techniques described herein can be employed to autonomously construct and evaluate plausible genetic family trees for individuals (including a target individual) that is derived at least in part from non-genetic data about those individuals. Such estimated measures of genetic relatedness could be used by practitioners to fill in gaps that may exist in sparse data sets of non-estimated measures of genetic relatedness data or to autonomously form plausible genetic family trees for individuals based solely on non-genetic data about the individuals. FIG. 21 shows an example system 100 which includes the use of such a trained ML classifier 2100 to generate estimated genetic relatedness data 2108 for use as source data 112. In the example of FIG. 21, one or more processors (such as processors 102) can be used to perform feature value computations 2104 that operates on non-genetic data about a plurality of individuals (see 2102) to compute a plurality of values for a plurality of features derived from the non-genetic data (see 2106). These features can be features that are found by machine learning to be predictive of and correlate to the estimated genetic relatedness data. The feature values 2106 can be applied to the trained ML classifier 2100 to predict estimated genetic relatedness data 2108 (such as estimated cM distances between a plurality of individuals). The estimated genetic relatedness data 2108 can be stored as source data 112 from which the family tree construction code 110 operates as described above. Example embodiments for training and implementing the ML classifier 2100 are described in the above-referenced and incorporated U.S. provisional patent application 63/432,623, filed Dec. 14, 2022, and entitled "Applied Artificial Intelligence for Estimating Measures of Genetic Relatedness Between Individuals Based on Non-Genetic Data About Individuals".

These and other modifications to the invention will be recognizable upon review of the teachings herein.

What is claimed is:

1. A system for forming one or more genetic family trees that connect a plurality of individuals based on measures of genetic relatedness between a plurality of the individuals, the system comprising:

one or more processors configured to:

group a plurality of the individuals into a cluster, wherein the cluster comprises only those of the individuals who are (1) are genetically related to a target individual according to first data and (2) genetically related to each other according to second data, wherein the first data comprises measures of genetic relatedness for a plurality of the individuals relative to the target individual, and wherein the second data comprises measures of genetic relatedness between a plurality of the individuals;

deconstruct the cluster into a tree structure based on the first data, wherein the tree structure comprises a plurality of nodes arranged hierarchically, wherein each node corresponds to an individual among the individuals from the cluster;

iteratively form one or more genetic family trees based on pairs of adjacent nodes from the tree structure until the nodes from the tree structure are positioned in the one or more genetic family trees based on the second data as applicable to the individuals corresponding to the pairs of adjacent nodes from the tree structure; and connect the target individual to the one or more genetic family trees based on the first data.

2. The system of claim 1 wherein the one or more processors are configured to use the second data to constrain a set of possible genetic relationships between individuals to consider when iteratively forming the one or more genetic family trees.

3. The system of claim 1 wherein the one or more processors are configured to use reference data to test the one or more genetic family trees for plausibility as nodes are positioned in the one or more genetic family trees, wherein the reference data defines a mapping of measures of genetic relatedness applicable to different types of genetic relationships.

4. The system of claim 1 wherein the cluster comprises a first cluster, and wherein the one or more processors are configured to:

group another plurality of the individuals into a second cluster, wherein the second cluster comprises only those of the individuals who are (1) are genetically related to the target individual according to the first data and (2) genetically related to each other according to the second data;

deconstruct the second cluster to augment the tree structure based on the first data, wherein the augmented tree structure comprises (1) a plurality of additional nodes arranged hierarchically, wherein each additional node corresponds to an individual among the individuals from the second cluster, and (2) a plurality branches, the branches including (i) a first branch based on the nodes corresponding to individuals from the first cluster and (ii) a second branch based on the additional nodes corresponding to the individuals from the second cluster; and perform the iterative formation of the one or more genetic family trees based on pairs of adjacent nodes from the augmented tree structure.

5. The system of claim 1 wherein the one or more processors are further configured to compute probabilities that are indicative of correctness for the one or more genetic family trees.

6. The system of claim 1 wherein the one or more processors are configured to concurrently perform a plurality of operations that are part of the grouping, deconstructing, iterative formation, and/or connect operations in parallel.

7. The system of claim 1 wherein the measures of genetic relatedness comprise centimorgan (cM) distances.

8. The system of claim 7 wherein the cM distances comprise measured cM distances.

9. The system of claim 7 wherein the cM distances comprise estimated cM distances.

10. The system of claim 1 wherein the one or more processors are configured to deconstruct the cluster into the tree structure by generating the tree structure so that the nodes are hierarchically arranged in the tree structure as a function of degree of genetic relatedness to the target individual according to the first data, and wherein the iteratively formed one or more genetic family trees are one or more genetic family trees for the individuals corresponding to the nodes of the tree structure.

11. The system of claim 10 wherein the one or more processors are further configured to augment the nodes in the tree structure by (1) determining corresponding sets of possible genetic relationships between the individuals corresponding to pairs of adjacent nodes in the tree structure according to the measures of genetic relatedness from the second data for the individuals corresponding to the pairs of adjacent nodes in the tree structure and (2) associating the nodes with the corresponding determined sets of possible genetic relationships between the individuals corresponding to the pairs of adjacent nodes in the tree structure.

12. The system of claim 1 wherein the one or more processors are configured to iteratively form the one or more genetic family trees based on pairs of adjacent nodes from the tree structure by creating and building a plurality of candidate genetic family trees for the individuals corresponding to the nodes of the tree structure from the pairs of adjacent nodes using the second data so that the individuals corresponding to the nodes of the tree structure populate the candidate genetic family trees in genetic relationship positions that are plausible in view of the measures of genetic relatedness from the second data for the individuals corresponding to the pairs of adjacent nodes in the tree structure; and wherein the one or more processors are configured to connect the target individual to one or more of the candidate genetic family trees based on the first data to generate one or more plausible genetic family trees for the target individual.

13. The system of claim 12 wherein the one or more processors are further configured to score the one or more plausible genetic family trees for the target individual according to a probability of being a true genetic family tree for the target individual.

14. The system of claim 1 wherein the one or more processors are configured to:

access source data, wherein the source data comprises data about a plurality of individuals including the first data and the second data;

determine, from the accessed source data, a plurality of individuals who are both (1) genetically related to the target individual according to the first data and (2) genetically related to each other according to the second data; and group the determined individuals into the cluster.

15. A method for forming one or more genetic family trees that connect a plurality of individuals based on measures of genetic relatedness between a plurality of the individuals, the method comprising:

grouping a plurality of the individuals into a cluster, wherein the cluster comprises only those of the individuals who are (1) are genetically related to a target individual according to first data and (2) genetically related to each other according to second data, wherein the first data comprises measures of genetic relatedness for a plurality of the individuals relative to the target individual, and wherein the second data comprises measures of genetic relatedness between a plurality of the individuals;

deconstructing the cluster into a tree structure based on the first data, wherein the tree structure comprises a plurality of nodes arranged hierarchically, wherein each node corresponds to an individual among the individuals from the cluster;

iteratively forming one or more genetic family trees based on pairs of adjacent nodes from the tree structure until the nodes from the tree structure are positioned in the one or more genetic family trees based on the second data as applicable to the individuals corresponding to the pairs of adjacent nodes from the tree structure; and connecting the target individual to the one or more genetic family trees based on the first data; and wherein the method steps are performed by one or more processors.

16. The method of claim 15 wherein the iteratively forming step comprises the one or more processors:

using the second data to constrain a set of possible genetic relationships between individuals to consider when iteratively forming the one or more genetic family trees.

17. The method of claim 15 further comprising the one or more processors using reference data to test the one or more genetic family trees for plausibility as nodes are positioned in the one or more genetic family trees, wherein the reference data defines a mapping of measures of genetic relatedness applicable to different types of genetic relationships.

18. The method of claim 15 wherein the cluster comprises a first cluster, the method further comprising the one or more processors:

grouping another plurality of the individuals into a second cluster, wherein the second cluster comprises only those of the individuals who are (1) are genetically related to the target individual according to the first data and (2) genetically related to each other according to the second data;

deconstructing the second cluster to augment the tree structure based on the first data, wherein the augmented tree structure comprises (1) a plurality of additional nodes arranged hierarchically, wherein each additional node corresponds to an individual among the individuals from the second cluster, and (2) a plurality branches, the branches including (i) a first branch based on the nodes corresponding to individuals from the first cluster and (ii) a second branch based on the additional nodes corresponding to the individuals from the second cluster; and performing the iteratively forming step based on pairs of adjacent nodes from the augmented tree structure.

19. The method of claim 15 further comprising the one or more processors computing probabilities that are indicative of correctness for the one or more genetic family trees.

20. The method of claim 15 wherein the one or more processors concurrently perform a plurality of operations that are part of the grouping, deconstructing, iteratively forming, and/or connecting steps in parallel.

21. The method of claim 15 wherein the measures of genetic relatedness comprise centimorgan (cM) distances.

22. The method of claim 21 wherein the cM distances comprise measured cM distances.

23. The method of claim 21 wherein the cM distances comprise estimated cM distances.

24. An article of manufacture comprising:

machine-readable code resident on a non-transitory computer-readable storage medium, wherein the code is configured for execution by one or more processors to cause the one or more processors to:

group a plurality of the individuals into a cluster, wherein the cluster comprises only those of the individuals who are (1) are genetically related to a target individual according to first data and (2) genetically related to each other according to second data, wherein the first data comprises measures of genetic relatedness for a plurality of the individuals relative to the target individual, and wherein the second data comprises measures of genetic relatedness between a plurality of the individuals;

deconstruct the cluster into a tree structure based on the first data, wherein the tree structure comprises a plurality of nodes arranged hierarchically, wherein each node corresponds to an individual among the individuals from the cluster;

iteratively form one or more genetic family trees based on pairs of adjacent nodes from the tree structure until the nodes from the tree structure are positioned in the one or more genetic family trees based on the second data as applicable to the individuals corresponding to the pairs of adjacent nodes from the tree structure; and connect the target individual to the one or more genetic family trees based on the first data.

\* \* \* \* \*